United States Patent
Bredenberg et al.

(10) Patent No.: US 10,543,203 B2
(45) Date of Patent: *Jan. 28, 2020

(54) ABUSE RESISTANT FORMULA

(71) Applicant: Emplicure AB, Uppsala (SE)

(72) Inventors: Susanne Bredenberg, Uppsala (SE); Anna Dahlgren, Uppsala (SE); Anders Sågström, Uppsala (SE); Håkan Engqvist, Uppsala (SE)

(73) Assignee: Emplicure AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/454,858

(22) Filed: Mar. 9, 2017

(65) Prior Publication Data

US 2017/0239229 A1    Aug. 24, 2017

Related U.S. Application Data

(63) Continuation of application No. 13/254,724, filed as application No. PCT/GB2010/000374 on Mar. 2, 2010, now Pat. No. 9,622,972.

(30) Foreign Application Priority Data

Mar. 4, 2009  (WO) ............... PCT/GB2009/000592

(51) Int. Cl.
*A61K 31/4468* (2006.01)
*A61K 9/16* (2006.01)

(52) U.S. Cl.
CPC ........ *A61K 31/4468* (2013.01); *A61K 9/1611* (2013.01); *A61K 9/1635* (2013.01); *A61K 9/1652* (2013.01); *A61K 9/1694* (2013.01)

(58) Field of Classification Search
CPC .............. A61K 31/4468; A61K 9/1694; A61K 9/1652; A61K 9/1611; A61K 9/1635
See application file for complete search history.

(56) References Cited

U.S. PATENT DOCUMENTS

| | | | |
|---|---|---|---|
| 4,861,599 A | 8/1989 | Springolo et al. | |
| 5,318,779 A | 6/1994 | Hakamatsuka et al. | |
| 5,443,812 A | 8/1995 | Nakajima et al. | |
| 5,902,591 A | 5/1999 | Herstein | |
| 6,123,925 A | 9/2000 | Barry et al. | |
| 6,334,856 B1 | 1/2002 | Allen et al. | |
| 6,342,249 B1 | 1/2002 | Wong et al. | |
| 6,503,231 B1 | 1/2003 | Prausnitz et al. | |
| 6,635,281 B2 | 10/2003 | Wong et al. | |
| 6,767,557 B2 * | 7/2004 | Ulrich ................... | A61K 9/0095 424/497 |
| 8,062,573 B2 | 11/2011 | Kwon | |
| 2002/0122828 A1 | 9/2002 | Liu | |
| 2003/0096002 A1 | 5/2003 | Borek et al. | |
| 2003/0118641 A1 | 6/2003 | Maloney et al. | |
| 2005/0163856 A1 | 7/2005 | Maloney et al. | |
| 2005/0273046 A1 | 12/2005 | Kwiatkowski et al. | |
| 2006/0024358 A1 | 2/2006 | Santini, Jr. et al. | |
| 2006/0057206 A1 | 3/2006 | Wong et al. | |
| 2006/0165787 A1* | 7/2006 | Moerck ................ | A61K 9/0053 424/468 |
| 2007/0053986 A1 | 3/2007 | Kuhn et al. | |
| 2007/0123837 A1 | 5/2007 | Adachi et al. | |
| 2007/0151485 A1 | 7/2007 | Hermansson et al. | |
| 2007/0212414 A1 | 9/2007 | Baichwal et al. | |
| 2007/0224129 A1 | 9/2007 | Guimberteau et al. | |
| 2007/0248656 A1 | 10/2007 | Galer | |
| 2007/0292526 A1 | 12/2007 | Barbe et al. | |
| 2008/0063725 A1 | 3/2008 | Guimberteau et al. | |
| 2008/0107720 A1 | 5/2008 | Walters et al. | |
| 2009/0200262 A1 | 8/2009 | Scholten et al. | |

FOREIGN PATENT DOCUMENTS

| | | |
|---|---|---|
| CN | 101104080 | 1/2008 |
| EA | 010826 | 12/2008 |
| EP | 265061 | 4/1988 |
| EP | 336014 | 6/1992 |
| EP | 947489 | 10/1999 |
| EP | 1285655 | 2/2003 |
| EP | 1674094 | 6/2006 |
| EP | 2100850 | 9/2009 |
| EP | 1429819 | 11/2010 |
| GB | 2307862 | 6/1997 |
| JP | H002268104 | 11/1990 |

(Continued)

OTHER PUBLICATIONS

Aguzzi et al., "Use of Clays as Drug Delivery Systems: Possibilities and Limitations," Applied Clay Science 36:22-36 (2007).
Cai, B., et al., "Self-setting Bioceramic Microscopic Protrusions for Transdermal Drug Delivery," J. Mater. Chem. B. 2:5992-5998 (2014).
Figiel, P., et al., "Properties of Alumina Ceramics Obtained by Conventional and Non-Conventional Methods for Sintering Ceramics," JAMME 48:29-34 (2011).
Martindale: The Complete Drug Reference, "Analgesics Anti-Inflammatory Drugs and Antipyretics," Pharm. Press, 35th ed. 90 (2007).
Wagh, A., "Chemically Bonded Phosphate Ceramics," Elsevier Ltd. Argonne National Laboratories, Sec. 1.1, 1-2 (2004).
Steveson et al., "Relationships Between Composition, Structure and Strength of Inorganic Polymers," J. Mater. Sci. 40:2023-2036 (2005).
Zheng et al., "Preparation of Geopolymer Precursors by Sol-gel Method and their Characterization," J. Mater. Sci. 44:3991-3996 (2009).

(Continued)

*Primary Examiner* — Snigdha Maewall
(74) *Attorney, Agent, or Firm* — Pepper Hamilton LLP

(57) ABSTRACT

There is provided a sustained-release pharmaceutical composition comprising a solid, continuous network comprising an excipient with a high mechanical strength, which network also comprises pores, within which pores is interspersed a mixture of an active ingredient and a film-forming agent, characterised in that said pores are formed during the production of the composition. Compositions of the invention find particularly utility as abuse-resistant formulations comprising opioid analgesics that may be employed in the treatment of chronic pain.

19 Claims, 10 Drawing Sheets

(56) References Cited

FOREIGN PATENT DOCUMENTS

| | | |
|---|---|---|
| JP | H07-188000 | 7/1995 |
| JP | 9030988 | 2/1997 |
| KR | 1020070042176 | 4/2007 |
| WO | 1989/005632 | 6/1989 |
| WO | 2001/072663 | 10/2001 |
| WO | 2003/090729 | 11/2003 |
| WO | 2003/092785 | 11/2003 |
| WO | 2004/024224 | 3/2004 |
| WO | 2004/028577 | 4/2004 |
| WO | 2004/040036 | 5/2004 |
| WO | 2004/058194 | 7/2004 |
| WO | 2005/037268 | 4/2005 |
| WO | 2005/039508 | 5/2005 |
| WO | 2005/051358 | 6/2005 |
| WO | 2006/000229 | 1/2006 |
| WO | 2006/017336 | 2/2006 |
| WO | 2006/083904 | 8/2006 |
| WO | 2006/089843 | 8/2006 |
| WO | 2006/096544 | 9/2006 |
| WO | 2007/074349 | 7/2007 |
| WO | 2008/080109 | 7/2008 |
| WO | 2008/105737 | 9/2008 |
| WO | 2008/105738 | 9/2008 |
| WO | 2008/105739 | 9/2008 |
| WO | 2008/118096 | 10/2008 |
| WO | 2008/142572 | 11/2008 |
| WO | 2009/113856 | 9/2009 |
| WO | 2010/096704 | 8/2010 |

OTHER PUBLICATIONS

Zoulgami et al., "Synthesis and Physico-Chemical Characterization of a Polysialate-Hydroxyapatite Composite for Potential Biomedical . . . ," Eur. Phys. J. AP 19:173-179 (2002).

Cai, B. et al., "Development and Evaluation of a Tampering Resistant Transdermal Fentanyl Patch." Int. J. Pharm. 488:102-107 (2015).

Mostafa, N.Y., "Characterization, Thermal Stability and Sintering of Hydroxyapatite Powders Prepared by Different Routes," Mater. Chem. Phys. 94:333-341 (2005).

Cai, B. et al., "Bioceramic Microneedles with Flexible and Self-Swelling Substrate," Eur. J. Pharm. Biopharm 94:404-410 (2015).

Gupta et al., "Formation of Physically Stable Amorphous Drugs by Milling with Neusilin," Journal of Pharm. Sci. 92 (3):536-551 (2003).

Petermann et al., "Alkali-Activated Geopolymers: A Literature Review", Air Force Research Laboratory, Jul. 2010.

Lin, Petroleum Engineering Construction, 31(5):9-11 (with English abstract) (2005).

The James Hutton Institute, "Halloysite and Kaolinite" www.claysandminerals.com/materials/halloysite, printed Dec. 23, 2014.

"Breast Cancer," American Cancer Society, www.cancer.org, retrieved Jan. 26, 2014, pp. 1-133.

Aulton, M.E., "Aulton's Pharmaceutics", 3rd ed., pp. 4-7 and 483-485 (2010).

Banga et al., "Microporation Applications for Enhancing Drug Delivery," Expert Opinion Drug Delivery 6(4):343-354 (2009).

Cai et al., "The Effect of Curing Conditions on Compression Strength and Porosity . . . " Ceram. Eng. Sci. Proc. 34:49-56 (2013).

Chretien, M.N., "Supramolecular Photochemistry in Zeolites: From Catalysts to Sunscreens," Pure and Applied Chemistry 79(1):1-20 (2007).

Davidovits, "30 Years of Successes and Failures in Geopolymer Applications," Geopolymer 2002 Conference, Oct. 2002, pp. 1-16.

De Silva et al., "The Role of Al2O3, SiO2 and Na2O on the Amorphous . . . " J. Aust. Ceram. Soc. 45(1):63-71 (2009).

DURAGESIS® Information Sheet, Janssen Pharmaceutical, Inc. 2009, revised 2012, 11 pages.

Forsgren et al., "A Ceramic Drug Delivery Vehicle for Oral Administration of Highly Potent Opioids", J. Pharm. Sci. 99(1):219-226 (2010).

Jamstorp et al., "Mechanically Strong Geopolymers Offer New Possibilities in Treatment of Chronic Pain", J. Control. Release 146:370-377 (2010).

Kawano et al., "Experimental Study on the Formation of Zeolites from Obsidian by Interaction with NaOH and KOH . . . ," Clays and Clay Minerals 45(3):365-377 (1997).

Lin et al., "A Study of Purified Montmorillonite Intercalated with 5-fluorouracil as Drug Carrier," Biomaterials 23:1981-1987 (2002).

Rowe et al., "Handbook of Pharmaceutical Excipients" 4th ed., pp. 89-92 (2003).

Rowe et al., "Handbook of Pharmaceutical Excipients" 6th ed., pp. 525-533 and 581-585 (2009).

Price et al., "In-vitro Release Characteristics of Tetracycline HCl< Khellin and Nicotinamide Adenine Dineculeotide . . . ," J. Microencapsulation 18(6):713-722 (2001).

Levis et al., "Use of Coated Microtubular Halloysite for the Sustained Release of Diltiazem Hydrochloride and Propranolol Hydrochloride," Int. J. Pharm 253:145-147 (2003).

Lasserre et al., "Ceramic Drug-Delivery Devices," Critical Reviews in Therapeutic Drug Carrier Systems 15(1):1-56 (1998).

Byrne et al., "Use of Porous Aluminosilicate Pellets for Drug Delivery," J. Microencapsulation 22(4):423-437 (2005).

Rimoli et al., "Synthetic Zeolites as a New Tool for Drug Delivery," J. Biomed. Mater. Res. 87A:156-164 (2008).

Cavallaro et al., "Drug Delivery Devices Based on Mesoporous Silicate," Drug Delivery 11:41-46 (2004).

Itokazu et ai., "Development of Porous Apatite Ceramic for Local Delivery of Chemotherapeutic Agents," J. Biomed. Mater. Res. 39:536-538 (1998).

Netz et al., "Potential Use of Gelcasting Hydroxyapatite Porous Ceramic as an Implantable Drug Delivery System," Int J. Pharmaceutics 213:117-125 (2001).

Krajewski et al., "Porous Ceramic Bodies for Drug Delivery," J Mat. Sci. Materials in Medicine 12:763-771 (2000).

Yao et al., "Fabrication of Hydroxyapatite Ceramics with Controlled Pore Characteristics by Slip Casting," J of Materials Science: Materials in Medicine 16:161-165 (2005).

Komlev et al., "Porouse Hydroxyapatite Ceramics of Bi-modal Pore Size Distribution," J. Materials Science: Materials in Medicine 13:295-299 (2002).

Byrne et al., "Use of Commerical Porous Ceramic Particles for Sustained Drug Delivery," Int. J. Pharmaceutics 246:61-73 (2002).

Gbureck et al., "Low Temperature Direct 3D Printed Bioceramics and Biocomposites as Drug Release Matrices," J. Controlled Release 122:173-180 (2007).

Medvecky et al., "Study of Controlled Tetracycline Release from Porous Calcium Phosphate/Polyhydroxybutyrate Composites," Chem. Pap. 61(6):477-484 (2007).

Paul et al., "Tricalcium Phosphate Delayed Release Formulation for Oral Delivery of Insulin: A Proof-of-Concept Study," J. Pharm. Sci. 97(2):875-82 (2008).

Duxson et al., "Geopolymer Technology: The Current State of the Art," J. Mater. Sci. 42:2917-2933 (2007).

\* cited by examiner

ABUSE RESISTANT FORMULA

This application is a continuation of U.S. patent application Ser. No. 13/254,724, now U.S. Pat. No. 9,622,972, which is a national stage application under 35 U.S.C. § 371 of PCT/GB2010/000374, filed Mar. 2, 2010, which claims priority benefit under 35 U.S.C. § 119 of PCT/GB2009/000592, filed Mar. 4, 2009.

FIELD OF THE INVENTION

This invention relates to new, non-abusable pharmaceutical compositions that provide for the controlled release of active ingredients, such as opioid analgesics, in the gastro-intestinal tract. The invention also relates to methods of manufacturing such pharmaceutical compositions.

BACKGROUND

The listing or discussion of an apparently prior-published document in this specification should not necessarily be taken as an acknowledgement that the document is part of the state of the art or is common general knowledge.

Opioids are widely used in medicine as analgesics, for example in the treatment of patients with severe pain, chronic pain, or to manage pain after surgery. Indeed, it is presently accepted that, in the palliation of more severe pain, no more effective therapeutic agents exist.

The term "opioid" is typically used to describe a drug that activates opioid receptors, which are found in the brain, the spinal cord and the gut. Three classes of opioids exist:
(a) naturally-occurring opium alkaloids. These include morphine and codeine;
(b) compounds that are similar in their chemical structure to the naturally-occurring opium alkaloids. These so-called semi-synthetics are produced by chemical modification of the latter and include the likes of diamorphine (heroin), oxycodone and hydrocodone; and
(c) truly synthetic compounds such as fentanyl and methadone. Such compounds may be completely different in terms of their chemical structures to the naturally-occurring compounds.

Of the three major classes of opioid receptors ($\mu$, $\kappa$ and $\delta$), opioids' analgesic and sedative properties mainly derives from agonism at the $\mu$ receptor.

Opioid analgesics are used to treat the severe, chronic pain of terminal cancer, often in combination with non-steroid anti-inflammatory drugs (NSAIDs), as well as acute pain (e.g. during recovery from surgery). Further, their use is increasing in the management of chronic, non-malignant pain.

Optimal management of chronic pain requires around-the-clock coverage. In this respect, opioid-requiring cancer patients are usually given slow-release opiates (slow-release morphine, oxycodone or ketobemidone, or transdermal fentanyl). Pharmaceutical formulations that are capable of providing a sustained release of active ingredients allow the patient to obtain this baseline analgesia with a minimal number of doses per day. This in turn improves patient compliance and minimizes interference with the individual's lifestyle and therefore quality of life.

Transdermal fentanyl drug delivery systems comprise patches (e.g. DURAGESIC®) that are applied to the skin to deliver that potent opioid analgesic, which is slowly absorbed through the skin into the systemic circulation. Pain may be relieved for up to three days from a single patch application.

However, such patches do not provide for a constant plasma level of opioid over the entire application period. This defect is an inevitable consequence of the fact that transdermal administration of fentanyl gives rise to the formation of a fentanyl depot in skin tissue. Serum fentanyl concentrations increase gradually following initial application of a patch, generally levelling off between 12 and 24 hours before reaching a saturation point, whereafter absorption of active ingredient remains relatively constant, with some fluctuation, for the remainder of the 72-hour application period.

Furthermore, firstly, in the design of sustained release formulations with extremely potent drugs, such as opioids, the risk for "dose dumping" has to be eliminated in view of the risk of severe and, on occasions, lethal side effects. Secondly, a perennial problem with potent opioid analgesics such as fentanyl is one of abuse by drug addicts. Addicts normally abuse pharmaceutical formulations by one or more of the following processes:
(a) extracting a large quantity of active ingredient from that formulation using acid and/or alcohol into solution, which is then injected intravenously. With most commercially-available pharmaceutical formulations, this can be done relatively easily, which renders them unsafe or "abusable";
(b) heating (and then smoking);
(c) crushing of tablet (and then snorting); and/or
(d) in the case of a patch, making a tea (and then drinking).

Thus, there is a clear unmet clinical need for an effective pharmaceutical formulation that is capable of treating e.g. severe pain via a sustained release of active ingredients (such as opioid analgesics), whilst at the same time minimising the possibility of dose dumping and/or abuse by addicts.

One solution to this problem that has been suggested is the incorporation of the active substance into a polymer matrix (see e.g. US2003/0118641 and US2005/0163856), which allows for the slow release of the active substance. However, this solution is not adequate as the drug abuser could either liberate the active substance from the polymer matrix by co-mixing with a solvent (either prior to ingestion, or the solvent may be co-ingested with the polymer matrix/active substance) or by crushing the polymer matrix.

Ceramics are becoming increasingly useful to the medical world, in view of the fact they are durable and stable enough to withstand the corrosive effect of body fluids.

For example, surgeons use bioceramic materials for repair and replacement of human hips, knees, and other body parts. Ceramics also are being used to replace diseased heart valves. When used in the human body as implants or even as coatings to metal replacements, ceramic materials can stimulate bone growth, promote tissue formation and provide protection from the immune system. Dental applications include the use of ceramics for tooth replacement implants and braces.

Ceramics are also known to be of potential use as fillers or carriers in controlled-release pharmaceutical formulations. See, for example, EP 947 489 A, U.S. Pat. No. 5,318,779, WO 2008/118096, Lasserre and Bajpai, *Critical Reviews in Therapeutic Drug Carrier Systems*, 15, 1 (1998), Byrne and Deasy, *Journal of Microencapsulation*, 22, 423 (2005) and Levis and Deasy, *Int. J. Pharm.*, 253, 145 (2003).

In particular, Rimoli et al, *J. Biomed. Mater. Res.*, 87A, 156 (2008), US patent application 2006/0165787 and international patent applications WO 2006/096544, WO 2006/017336 and WO 2008/142572 all disclose various ceramic substances for controlled release of active ingredients, with the latter two documents being directed in whole or in part to opioid analgesics, with the abuse-resistance being imparted by the ceramic structures' mechanical strength.

Methods employed in these documents typically involve the incorporation of active ingredients into pre-formed porous ceramic materials comprising e.g. porous halloysite, kaolin, titanium oxide, zirconium oxide, scandium oxide, cerium oxide and yttrium oxide. In this respect, loading of active ingredient typically comprises soaking, extrusion-spheronization and/or cryopelletization. It is known to be difficult to infuse drug into a pre-formed porous ceramic structure. Indeed, in the case of opioids, it is considered that such active ingredient-incorporation methodology will not enable the loading of sufficient active ingredient to provide appropriate doses for effective therapeutic pain management, over a prolonged time, given that infusion of active ingredient into preformed pores is a difficult thing to do.

In WO 2008/142572, drugs are incorporated during the formation of a ceramic carrier using chemically bonded ceramics, such as calcium aluminate or calcium silicate. Although this leads to a higher amount of drug incorporation than is typically the case for preformed ceramic materials, the mechanical strength and the chemical stability of the ceramic structures described in WO 2008/142572 is, relatively speaking, limited, especially in acidic conditions.

Furthermore, although the formulations described in the aforementioned documents may further include e.g. hydrophobic polymers, the methods employed involve the pre- or post-treating of porous ceramic materials with such materials either before or after (as appropriate) the ceramic structure is combined with the active ingredient, which is contained within the porous matrix of the ceramic.

DISCLOSURE OF THE INVENTION

Figure 1:
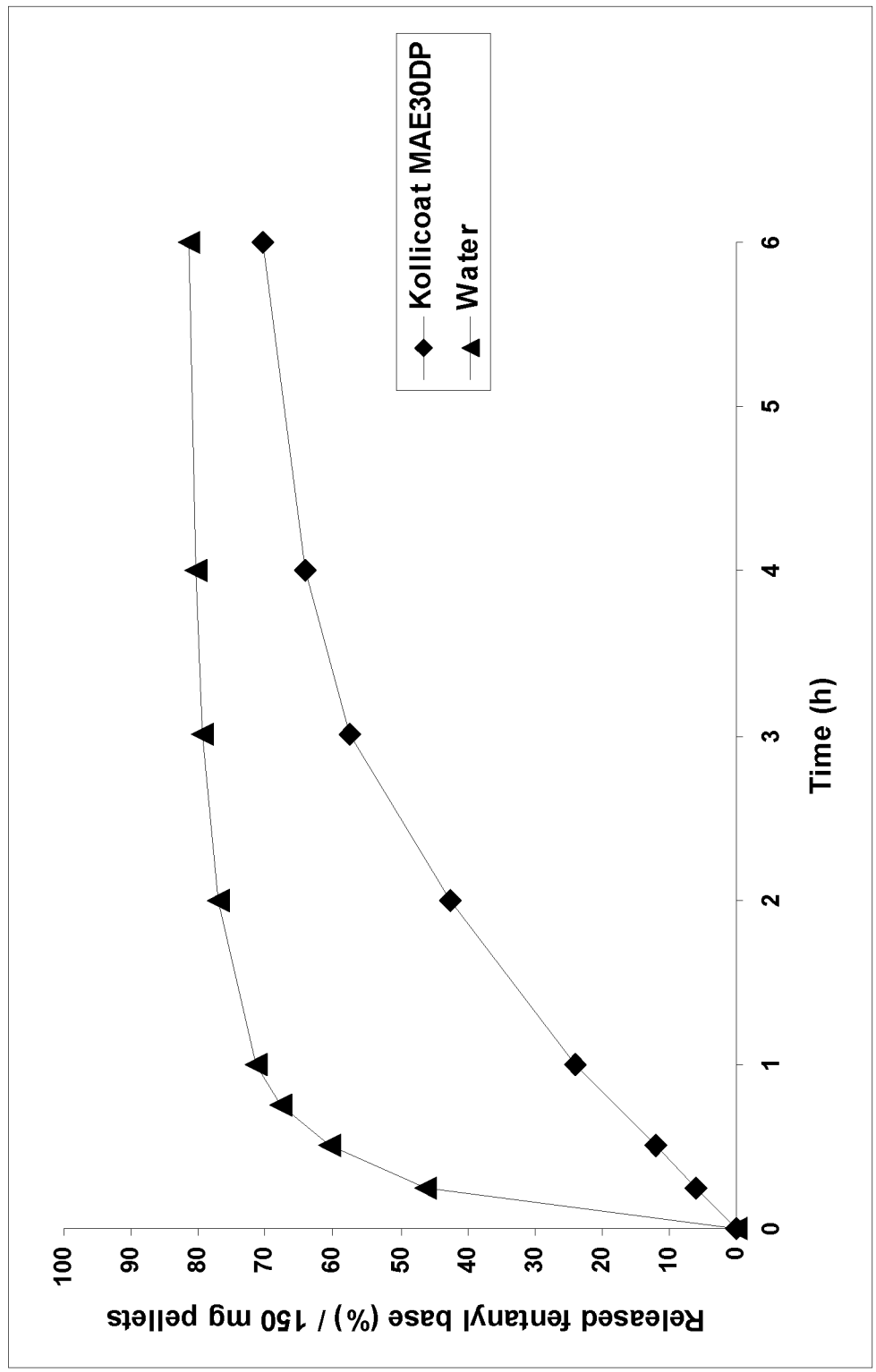
FIG. 1 shows the release profile of fentanyl base in phosphate buffer (pH 6.8) from ceramic pellets made from aluminium silicate (halloysite), employing either Kollicoat MAE 30 DP or water as the granulation liquid.

According to the invention, there is provided a sustained-release pharmaceutical composition comprising a solid, continuous, porous network, which network comprises:
(a) a (preferably inorganic) excipient with a high mechanical strength; and
(b) pores, or voids between areas of said excipient in the network, within which pores is interspersed a mixture of an active ingredient and a film-forming agent, characterised in that said pores containing said mixture of active ingredient and film-forming agent are formed during the production of the composition. Compositions comprising such features are hereinafter referred to together as "the compositions of the invention".

The term "sustained-release" is employed herein synonymously with the term "controlled-release", and will be understood by the skilled person to include compositions that provide, and/or are adapted to provide, for a "sustained", a "prolonged" and/or an "extended" release of drug (in which drug is released at a sufficiently retarded rate to produce a therapeutic response over a required period of time).

We have advantageously found that compositions of the invention provide for release of active ingredient that is substantially uniform and/or nearly constant over an extended period of time. In one embodiment, a nearly constant rate of release can vary over a dose interval from about 6 hours to about 2 days. Constant release may further be defined as a composition being capable of maintaining a steady state concentration in a body fluid not deviating more than about 20% (e.g. about 10%) from the mean value during the dose interval. The release rate may be maintained over a long time period, corresponding approximately to the passage of time taken between initial oral administration of a composition of the invention and excretion of the carrier material from the body, such as between about 5 and about 24 (such as about 15) hours.

Active ingredients that may be employed in compositions of the invention preferably include substances from various pharmacological classes, e.g. antibacterial agents, antihistamines and decongestants, anti-inflammatory agents, antiparasitics, antivirals, local anaesthetics, antifungals, amoebicidals or trichomonocidal agents, analgesics, antianxiety agents, anticlotting agents, antiarthritics, antiasthmatics, anticoagulants, anticonvulsants, antidepressants, antidiabetics, antiglaucoma agents, antimalarials, antimicrobials, antineoplastics, antiobesity agents, antipsychotics, antihypertensives, auto-immune disorder agents, anti-impotence agents, anti-Parkinsonism agents, anti-Alzheimer's agents, antipyretics, anticholinergics, anti-ulcer agents, blood-glucose-lowering agents, bronchodilators, central nervous system agents, cardiovascular agents, cognitive enhancers, contraceptives, cholesterol-reducing agents, agents that act against dyslipidermia, cytostatics, diuretics, germicidials, H2 blockers, proton pump inhibitors, hormonal agents, anti-hormonical agents, hypnotic agents, inotropics, muscle relaxants, muscle contractants, physic energizers, sedatives, sympathomimetics, vasodilators, vasocontrictors, tranquilizers, electrolyte supplements, vitamins, uricosurics, cardiac glycosides, membrane efflux inhibitors, membrane transport protein inhibitors, expectorants, purgatives, contrast materials, radiopharmaceuticals, imaging agents, peptides, enzymes, growth factors, vaccines, mineral trace elements.

Active ingredients that may be employed in compositions of the invention preferably include any that are open to abuse potential, such as those that are useful in the treatment of acute or chronic pain, attention deficit hyperactivity disorders (ADHD), anxiety and sleep disorders, as well as growth hormones (e.g. erythropoietin), anabolic steroids, etc. A full list of potentially abusable substances may be found easily by the skilled person, for example see the active ingredients listed on the following weblink: http://www.deadiversion.usdoj.gov/schedules/alpha/alpha-betical.htm.

Non-opioid drug substances that may be specifically mentioned include psychostimulants, such as modafinil, amphetamine, dextroamphetamine, methamphetamine and hydroxyamphethamine and, more preferably, methylfenidate; benzodiazepines, such as bromazepam, camazepam, chlordiazepoxide, clotiazepam, cloxazepam, delorazepam, estazolam, fludiazepam, flurazepam, halazepam, haloxazepam, ketazolam, lormetazepam, medazepam, nimetazepam, nordiazepam, oxazolam, pinazepam, prazepam, temazepam, tetrazepam and, more preferably, alprazolam, clonazepam, diazepam, flunitrazepam, lorazepam, midazolam, nitrazepam, oxazepam and triazolam; and other, non-benzodiazepine sedatives (e.g. short-acting hypnotics), such as zaleplon, zolpidem, zopiclone and eszopiclone.

Compositions of the invention may also find utility in the formulation of pharmaceuticals where crushing of a tablet may put the patient at risk, or may increase the risk for adverse effects and/or an unpleasant taste. That is to say, those active ingredients where avoidance of one or more of the following is desirable:
i) a tablet being chewed before being swallowed;
ii) accidental destruction during passage through the gastrointestinal tract;
iii) release of drug content as a consequence of concomitant intake of, for instance, alcoholic beverages, which may destroy the controlled release functionality of a tablet formulation; and/or
iv) ex vivo tampering, i.e. crushing for subsequent abuse (vide infra), or for ease of subsequent swallowing, which may result in destruction of the functionality of the formulated drug.

Such drugs will be well known to the skilled person, but may also be found for example on the weblink http://www.ismp.org/Tools/DoNotCrush.pdf. Such drugs include those that are used for the treatment of a variety of disorders where slow release formulations are beneficial, including drugs that are employed in the treatment of cardiovascular diseases (hypertension, heart failure), diabetes, asthma, CNS disorders and urogenital disorders, as well as antibiotics.

However, preferred pharmaceutically-active ingredients that may be employed in compositions of the invention include opioid analgesics. The term "opioid analgesic" will be understood by the skilled person to include any substance, whether naturally-occurring or synthetic, with opioid or morphine-like properties and/or which binds to opioid receptors, particularly the p-opioid receptor, having at least partial agonist activity, thereby capable of producing an analgesic effect. The problems of potential formulation tampering and drug extraction by drug addicts are particularly prominent with opioids.

Opioid analgesics that may be mentioned include opium derivatives and the opiates, including the naturally-occurring phenanthrenes in opium (such as morphine, codeine, thebaine and Diels-Alder adducts thereof) and semisynthetic derivatives of the opium compounds (such as diamorphine, hydromorphone, oxymorphone, hydrocodone, oxycodone, etorphine, nicomorphine, hydrocodeine, dihydrocodeine, metopon, normorphine and N-(2-phenylethyl)normorphine). Other opioid analgesics that may be mentioned include fully synthetic compounds with opioid or morphine-like properties, including morphinan derivatives (such as racemorphan, levorphanol, dextromethorphan, levallorphan, cyclorphan, butorphanol and nalbufine); benzomorphan derivatives (such as cyclazocine, pentazocine and phenazocine); phenylpiperidines (such as pethidine (meperidine), fentanyl, alfentanil, sufentanil, remifentanil, ketobemidone, carfentanyl, anileridine, piminodine, ethoheptazine, alphaprodine, betaprodine, 1-methyl-4-phenyl-1,2,3,6-tetrahydropyridine (MPTP), diphenoxylate and loperamide), phenylheptamines or "open chain" compounds (such as methadone, isomethadone, propoxyphene and levomethadyl acetate hydrochloride (LAAM)); diphenylpropylamine derivatives (such as dextromoramide, piritramide, bezitramide and dextropropoxyphene); mixed agonists/antagonists (such as buprenorphine, nalorphine and oxilorphan) and other opioids (such as tilidine, tramadol and dezocine). Further opioid analgesics that may be mentioned include allylprodine, benzylmorphine, clonitazene, desomorphine, diampromide, dihydromorphine, dimenoxadol, dimepheptanol, dimethylthiambutene, dioxaphetyl butyrate, dipipanone, eptazocine, ethylmethylthiambutene, ethylmorphine, etonitazene, hydroxypethidine, levophenacylmorphan, lofentanil, meptazinol, metazocine, myrophine, narceine, norpipanone, papvretum, phenadoxone, phenomorphan, phenoperidine and propiram.

More preferred opioid analgesics include buprenorphine, alfentanil, sufentanil, remifentanil and, particularly, fentanyl.

Active ingredients listed above may be formulated in compositions of the invention in any specific combination.

Active ingredients may further be employed in salt form or any other suitable form, such as e.g. a complex, solvate or prodrug thereof, or in any physical form such as, e.g., in an amorphous state, as crystalline or part-crystalline material, as co-crystals, or in a polymorphic form or, if relevant, in any stereoisomeric form including any enantiomeric, diastereomeric or racemic form, or a combination of any of the above.

Pharmaceutically-acceptable salts of active ingredients that may be mentioned include acid addition salts and base addition salts. Such salts may be formed by conventional means, for example by reaction of a free acid or a free base form of an active ingredient with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of active ingredient in the form of a salt with another counter-ion, for example using a suitable ion exchange resin.

Examples of pharmaceutically acceptable addition salts include those derived from mineral acids, such as hydrochloric, hydrobromic, phosphoric, metaphosphoric, nitric and sulphuric acids; from organic acids, such as tartaric, acetic, citric, malic, lactic, fumaric, benzoic, glycolic, gluconic, succinic, arylsulphonic acids; and from metals such as sodium, magnesium, or preferably, potassium and calcium.

The (preferably inorganic) excipient may be designed to be inert in the following ways:

(a) acid resistance, a necessary attribute for the excipient to possess when passing through the stomach following oral administration. In this respect, excipients as described herein show an insignificant degree (e.g. less than 1%) of chemical degradation or decomposition in aqueous acid milieu (at pH values between about 0.1 and about of 4.0) at temperatures in excess of room temperature (e.g. up to about 50° C.);
(b) general physico-chemical stability under normal storage conditions, including temperatures of between about minus 80 and about plus 50° C. (preferably between about 0 and about 40° C. and more preferably room temperatures, such as about 15 to about 30° C.), pressures of between about 0.1 and about 2 bars (preferably at atmospheric pressure), relative humidities of between about 5 and about 95% (preferably about 10 to about 75%), and/or exposure to about 460 lux of UV/visible light, for prolonged periods (i.e. greater than or equal to six months). Under such conditions, excipients as described herein may be found to be less than about 5%, such as less than about 1% chemically degraded/decomposed, as above;
(c) particularly importantly when the active ingredient that is employed is an opioid analgesic, general physico-chemical stability under acidic, alkaline and/or alcoholic (e.g. ethanolic) conditions at room temperature and/or under at elevated temperatures (e.g. up to about 100° C.), which may result in less than about 15% degradation, so avoiding the possibility of deliberate ex vivo extraction of drug for intended abuse (e.g. by acid or alcohol extraction, followed by injection, or heating a composition of the invention and then an opioid addict inhaling the vapour or smoke that is given off); and
(d) again, particularly importantly when the active ingredient that is employed is an opioid analgesic, general physical stability, for example with a high mechanical impact strength, so reducing the possibility of mechanical grinding or milling with a view to extraction of active ingredient as defined in (c) above, or by an opioid addict sniffing a resultant powder directly.

With reference to (d) above, it is preferred in this respect that the excipient exhibits a compressive strength of greater than about 10 MPa, such as 50 MPa (preferably more than about 100 MPa, e.g. about 400 MPa) on micro- and nanostructure level, which is high enough to withstand breakdown of the material at the microstructure level, i.e. of less than about 200 μm.

In this respect, by (preferably inorganic) excipient of "high mechanical strength" we also include that the structure of that excipient maintains its overall integrity (e.g. shape, size, porosity, etc) when a force of about 1 kg-force/cm² (9 newtons/cm²), such as about 5 kg-force/cm² (45 newtons/cm²), such as about 7.5 kg-force/cm², e.g. about 10.0 kg-force/cm², preferably about 15 kg-force/cm², more preferably about 20 kg-force/cm², for example about 50 kg-force/cm², especially about 100 kg-force/cm² or even about 125 kg-force/cm² (1125 newtons/cm²) is applied using routine mechanical strength testing techniques known to the skilled person (for example using a so-called "compression test" or "diametral compression test", employing a suitable instrument, such as that produced by Instron (the "Instron Test", in which a specimen is compressed, deformation at various loads is recorded, compressive stress and strain are calculated and plotted as a stress-strain diagram which is used to determine elastic limit, proportional limit, yield point, yield strength and (for some materials) compressive strength)). When the structure of the excipient is particulate, at least about 40% (e.g. at least about 50%, such as at least about 60% preferably, at least about 75%, and more preferably at least about 90%) of the particles (whether primary or secondary particles) maintain their integrity under these conditions.

The excipient of high mechanical strength is preferably inorganic, but may also comprise an inert polymeric material, such as a polyacrylates or a copolymer thereof, a polyethylene glycol, a polyethylene oxide, a polyethylene, a polypropylene, a polyvinyl chlorides, a polycarbonate, a polystyrene and the like.

Preferably, the excipient of high mechanical strength is based on one or more ceramic materials.

The term "ceramic" will be understood to include compounds formed between metallic and nonmetallic elements, frequently oxides, nitrides and carbides that are formed and/or processable by some form of curing process, which often includes the action of heat. In this respect, clay materials, cement and glasses are included within the definition of ceramics (Callister, "*Material Science and Engineering, An Introduction*" John Wiley & Sons, 7$^{th}$ edition (2007)).

It is preferred that the ceramic material that is employed is based upon an aluminate, such as a calcium aluminate or, more preferably, a silicate such as an aluminium (alumino) silicate. However, it may also be an oxide and/or a double oxide, and/or a nitride and/or a carbide of any of the elements silicon, aluminium, carbon, boron, titanium, zirconium, tantalum, scandium, cerium, yttrium or combinations thereof.

Preferred materials include aluminium silicate and/or aluminium silicate hydrate (crystalline or amorphous). Non-limiting examples include kaolin, dickite, halloysite, nacrite, ceolite, illite or combinations thereof, preferably halloysite. The grain size of the ceramic material (e.g. aluminium silicate) may be below about 500 μm, preferably below about 100 μm, and particularly below about 20 μm, as measured by laser diffraction in the volume average mode (e.g. Malvern master size). The grains may be of any shape (e.g. spherical, rounded, needle, plates, etc.).

Ceramics may comprise chemically bonded ceramics (non-hydrated, partly hydrated or fully hydrated ceramics, or combinations thereof). Preferred chemical compositions include those based on chemically bonded ceramics, which during hydration consume a controlled amount of water. The preferred systems available are those based on aluminates and silicates, both of which consume a great amount of water. Phases such CA2, CA, CA3 and C12A7, and C2S and C3S in crystalline or amorphous state (C=CaO, A=Al$_2$O$_3$, SiO$_2$=S, according to common cement terminology) may be used, which are readily available. The calcium aluminate and/or calcium silicate phases may be used as separate phase or as mixtures of phases. The above-mentioned phases, all in non-hydrated form, act as the binder phase (the cement) in the carrier material when hydrated.

The grain size of any ceramic precursor powder particles may be below about 100 μm, preferably between about 1 μm and about 20 μm. This is to enhance hydration. Such precursor material may be transformed into a nano-size microstructure during hydration. This reaction involves dissolution of the precursor material and repeated subsequent precipitation of nano-size hydrates in the water (solution) and upon remaining non-hydrated precursor material. This reaction favourably continues until all precursor materials have been transformed and/or to a porosity determined by partial hydration using the time and temperature, as well as the H$_2$O in liquid and/or humidity, selected.

Alternatively, an inorganic excipient of high mechanical strength may be based on one or more geopolymer materials.

The term "geopolymer" will be understood by those skilled in the art to include or mean any material selected from the class of synthetic or natural aluminosilicate materials which may be formed by reaction of an aluminosilicate precursor material (preferably in the form of a powder) with an aqueous alkaline liquid (e.g. solution), preferably in the presence of a source of silica.

The term "source of silica" will be understood to include any form of a silicon oxide, such as $SiO_2$, including a silicate. The skilled person with appreciate that silica may be manufactured in several forms, including glass, crystal, gel, aerogel, fumed silica (or pyrogenic silica) and colloidal silica (e.g. Aerosil).

Suitable aluminosilicate precursor materials are typically (but not necessarily) crystalline in their nature include kaolin, dickite, halloysite, nacrite, zeolites, illite, preferably dehydroxylated zeolite, halloysite or kaolin and, more preferably, metakaolin (i.e. dehydroxylated kaolin). Dehydroxylation (of e.g. kaolin) is preferably performed by calcining (i.e. heating) of hydroxylated aluminosilicate at temperatures above 400° C. For example, metakaolin may be prepared as described by Stevenson and Sagoe-Crentsil in *J. Mater. Sci.*, 40, 2023 (2005) and Zoulgami et al in *Eur. Phys J. AP,* 19, 173 (2002), and/or as described hereinafter. Dehydroxylated aluminosilicate may also be manufactured by condensation of a source of silica and a vapour comprising a source of alumina (e.g. $Al_2O_3$).

If provided in the form of a powder, the grain size of the aluminosilicate precursor particles are below about 500 μm, preferably below about 100 μm, more preferred below about 30 μm.

In the formation of geopolymer materials, such precursor materials may be dissolved in an aqueous alkaline solution, for example with a pH value of at least about 12, such as at least about 13. Suitable sources of hydroxide ions include strong inorganic bases, such as alkali or alkaline earth metal (e.g. Ba, Mg or, more preferably, Ca or, especially Na or K, or combinations thereof) hydroxides (e.g. sodium hydroxide). The molar ratio of metal cation to water can vary between about 1:100 and about 10:1, preferably between about 1:20 and about 1:2.

A source of silica (e.g. a silicate, such as $SiO_2$) is preferably added to the reaction mixture by some means. For example, the aqueous alkaline liquid may comprise $SiO_2$, forming what is often referred to as waterglass, i.e. a sodium silicate solution. In such instances, the amount $SiO_2$ to water in the liquid is preferably up to about 2:1, more preferably up to about 1:1, and most preferably up to about 1:2. The aqueous liquid may also optionally contain sodium aluminate.

Silicate (and/or alumina) may alternatively be added to the optionally powdered aluminosilicate precursor material, preferably as fume silica (microsilica; AEROSIL® silica). The amount that may added is preferably up to about 30 wt %, more preferably up to about 5 wt. % of the aluminosilicate precursor.

The presence of free hydroxide ions in this intermediate alkaline mixture, causes aluminium and silicon atoms from the source material(s) to be dissolved. The geopolymer materials may then be formed by allowing the resultant mixture to set (cure or harden), during which process the aluminium and silicon atoms from the source materials reorientate to form a hard (and at least largely) amorphous geopolymeric material. Curing may be performed at room temperature, at elevated temperature or at reduced temperature, for example at around or just above ambient temperature (e.g. between about 20° C. and about 90° C., such as around 40° C.). The hardening may also be performed in any atmosphere, humidity or pressure (e.g. under vacuum or otherwise). The resultant inorganic polymer network is in general a highly-coordinated 3-dimensional aluminosilicate gel, with the negative charges on tetrahedral $Al^{3+}$ sites charge-balanced by alkali metal cations.

In this respect, an geopolymer-based excipient of high mechanical strength may be formed by mixing a powder comprising the aluminosilicate precursor and an aqueous liquid (e.g. solution) comprising water, a source of hydroxide ions as described hereinbefore and the source of silica (e.g. silicate), to form a paste. The ratio of the liquid to the powder is preferably between about 0.2 and about 20 (w/w), more preferably between about 0.3 and about 10 (w/w). Calcium silicate and calcium aluminate may also be added to the aluminosilicate precursor component.

In accordance with the invention, the pores of the network of compositions of the invention, within which the mixture of active ingredient and film-forming agent is dispersed, are formed during production of the composition and are therefore essentially "secondary pores". In this respect, although primary particles of the (preferably inorganic) excipient of high mechanical strength may be porous in their own right (and therefore comprise "primary" pores), the network comprises, essentially, secondary pores (or voids) that are formed during the formation of larger, secondary particles consisting essentially of the excipient.

Such secondary pores may for example be formed by chemical interactions (e.g. "bonding") between the surfaces of primary particles of (preferably inorganic) excipients, such as ceramics, and may, for example, result from exposure to one or more chemical reagents that cause a physical and/or chemical transformation (such as a partial dissolution) at, and subsequent physical and/or chemical bonding together of, those surfaces (which may in itself result as a consequence of some other physico-chemical process such as drying, curing, etc.), giving rise to said pores/voids. Such chemical reagents may be mixed together with active ingredient and/or film forming agent during preparation of a composition of the invention. However, such secondary pores are not necessarily formed in this way and bonding together of primary particles of excipient may also be physical and/or mechanical, or may be formed during the production of a three-dimensional, chemically bonded ceramic network as described hereinbefore, in the presence of a mixture of active ingredient and film forming agent.

Thus, a sustained-release pharmaceutical composition is provided, comprising a solid, continuous three-dimensional network comprising particles of a (preferably inorganic) excipient with a high mechanical strength, which particles are bonded together to form secondary pores or voids, and a, preferably pre-formed, preferably homogeneous (as defined hereinafter) mixture of an active ingredient and a film-forming agent, which mixture is interspersed within said voids.

Mixtures of active ingredient and film-forming agent may also be interspersed between particles (of whatever size) of (preferably inorganic) excipients of high mechanical strength, and therefore be located between the exterior surfaces and, possibly but not essentially, within the interior of such particles.

However, the secondary particles of the excipient may consist essentially of that excipient. By "consisting essentially" of the excipient, we mean that the particles comprise at least about 40%, such as about 55%, for example about 75% and especially about 95% by weight of that excipient. Further, we also include that at least about 40%, such as about 55%, for example about 75% and especially about 80%, e.g. about 90%, such as at least about 95% (e.g. about 98%) by weight of the mixture of active ingredient and film-forming agent are located within (secondary) pores that are an essential feature of the network.

We have advantageously found that providing a composition of the invention in the manner claimed may impart controlled-release properties as mentioned hereinbefore. The film-forming agent component may also further advantageously increase the mechanical strength of compositions of the invention. Both of these features provide advantages associated with the prevention of dose dumping and potential drug abuse by ex vivo extraction of the active ingredient, when the latter comprises an opioid analgesic.

The admixing of active ingredient and film-forming agent may take place prior to or during interspersion within the excipient, such that the majority (i.e. greater than about 50%, such as greater than about 75%) of those components are added to the excipient at essentially the same time, and not separately, such that there is substantially uniform blending/inter-mixing of the components as defined above. Most preferably, there is a substantially uniform content (i.e. variations of no more than about ±50%, such as about ±40%, preferably about ±30%, more preferably about ±20% and particularly about ±10%) of the active ingredient throughout the film-forming agent, and/or there is no particular location within the film-forming agent where there is a substantially greater concentration of the active ingredient to provide a homogeneous distribution.

When used herein, the term "film-forming agent" refers to a substance that is capable of forming a film over (or within), or coating over, another substance (which may be in particulate form).

It is preferred that the film-forming agent is a material that is capable of providing a sustained-release, delayed-release or, preferably, enteric-release coating (i.e. an enteric coating material). Substances that are capable of providing an enteric coating are thus those that may be employed in peroral pharmaceutical formulations as a barrier to prevent or minimise release of active ingredient prior to such formulations reaching the small intestine.

In this respect, it is preferred that the film-forming agent is a polymer. Examples of polymers that may be employed as film-forming agents include, without limitation: alkylcellulose polymers (e.g. ethylcellulose polymers), and acrylic polymers (e.g. acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamid copolymer, poly(methyl methacryate), poly(methacrylic acid) (anhydride), methyl methacrylate, polymethacrylate, methyl methacrylate copolymer, poly(m-ethyl methacrylate), poly(methyl methacrylate) copolymer, polyacryamide, aminoalkyl methacrylate copolymer, poly(methacrylic acid anhydride), and glycidyl methacrylate copolymers). The polymer may also be a mixture of polymers. Typically, the molecular weight (weight average and/or number average) of the polymer is 1,000 to 10,000,000, 10,000 to 1,000,000, preferably 50,000 to 500,000 g/mol, as measured by gel permeation chromatography.

Preferred polymers include the alkyl cellulose polymers and acrylic polymers described herein.

Preferably, the film-forming agent comprises polymer that exhibits anionic character and/or is weakly acidic (for example that have a pH of less than 7, and preferably less than 5).

The most preferred polymer includes that marketed under the trademark Kollicoat®. Kollicoat® comprises a copolymer derived from methacrylic acid and ethyl acrylate. Kollicoat® MAE 30 DP (BASF) is a copolymer of methacrylic acid/ethyl acrylate (1:1), and is available as an aqueous dispersion or powder. Other polymers that may be mentioned include those marketed under the trademark Eudragit®, which are neutral methacrylic polymers with acid or alkaline groups.

Compositions of the invention may also comprise a pelletisation aid material. A pelletisation aid material may be defined as a material that is capable of controlling the distribution of granulating liquid through the wet powder mass during pelletisation and to modify the rheological properties in the mixture. Suitable pelletisation aid materials include hydroxypropylmethylcellulose (HPMC), hydroxyethylcellulose (HEC) and, preferably, microcrystalline cellulose. If present, the pelletisation aid material is preferably employed in an amount of between 0.5 and 50% by weight based upon the total weight of the tablet formulation. A preferred range is from 1 to 20%, such as from about 2.0 to about 12% (e.g. about 10%) by weight.

Compositions of the invention may be prepared by way of a variety of routine techniques, and using standard equipment, known to the skilled person, including mixing together the active ingredient, the film-forming agent and the (preferably inorganic) excipient of high mechanical strength.

Standard mixing equipment may be used for mixing together components of compositions of the invention. The mixing time period is likely to vary according to the equipment used, and the skilled person will have no difficulty in determining by routine experimentation a suitable mixing time for a given combination of ingredient(s).

The active ingredient and the film-forming agent (or the active ingredient interspersed with the film-forming agent) may be mixed with the excipient (e.g. ceramic) by way of a variety of techniques, such as introduction by way of a sol-gel process, as a solution, a slurry, a paste or a putty. The introduction of the mixture comprising the active ingredient and the film forming agent an inorganic excipient may be followed by some sort of "curing" to form the pores that are an essential feature of a composition of the invention, and in which the mixture of active ingredient and the film-forming agent resides. It is during this process that the porous network comprising the excipient may be formed.

A preferred process for the formation of compositions of the invention involves the mixing together of an inorganic excipient of high mechanical strength (e.g. ceramic material) and active substance, and then adding the film-forming agent along with, or in, a liquid, such as an aqueous solvent (e.g. water), so providing a wet granulate.

Wet granulation techniques are well known to those skilled in the art and include any technique involving the massing of a mix of dry primary powder particles using a granulating fluid, which fluid comprises a volatile, inert solvent, such as water, optionally in the presence of a pelletisation aid material.

The product obtained by the above-mentioned process may further be adapted by:
(I) extrusion of the granulate (in cases where granulation takes place);
(II) spheronisation (forcing a wet mass through a sieve to produce pellets);
(III) drying; and/or
(IV) (if necessary) hardening by way of heat,
using routine techniques in all cases.

In the process for formation of compositions of the invention comprising geopolymers, preformed geopolymer may be reacted together further aluminosilicate precursor and aqueous alkaline liquid (e.g. solution), preferably in the presence of a source of silica (as hereinbefore described), also in the presence of the active ingredient and the film-forming agent (or the active ingredient interspersed with the film-forming agent) as hereinbefore described. For compositions of the invention comprising geopolymers, curing may be performed by allowing the resultant mixture to harden into any given shape, e.g. blocks, pellets, granules or a powder. In this respect, the mixture may be transferred into moulds and left to set as pellets/granules or alternatively (e.g. preferably) pellets/granules may be manufactured using an appropriate extrusion-spheronization technique. Here, the formed paste (powder and liquid mixture) may be extruded through an orifice. The size of the orifice may be from about 10 μm up to about 30 mm, preferably from about 100 μm to about 1 mm. The formed extrudate may then be placed in a spheronizer, which is typically a vertical hollow cylinder with a horizontal rotating disk located inside. When the disk is spun, the extrudate is broken into uniform lengths and gradually formed into spherical pellets, which may then be left to harden as described hereinbefore.

In the processes described above, film-forming agent is preferably added as an aqueous dispersion. Further, primary particles of ingredients (e.g. opioid analgesic) may be processed by techniques, such as grinding, dry milling, wet milling, precipitation, etc, prior to granulation.

In all cases, suitable pellet/granule sizes are in the range of about 0.05 mm to about 3.0 mm (e.g. about 2.0 mm, such as about 1.7 mm), and preferably about 0.1 mm (e.g. about 0.2 mm) to about 1.6 mm (e.g. about 1.5 mm), such as about 1.0 mm.

Compositions of the invention may further comprise one or more further commonly-employed pharmaceutical excipients. Suitable excipients include inactive substances that are typically used as a carrier for the active ingredients in medications. Suitable excipients also include those that are employed in the pharmaceutical arts to bulk up pharmaceutical compositions that employ very potent active ingredients, to allow for convenient and accurate dosing. Alternatively, excipients may also be employed in manufacturing processes of the compositions of the invention to aid in the handling of the active ingredient concerned.

In this respect, pharmaceutically-acceptable excipients include filler particles, by which we include particles that do not take participate chemically in the process during which the composition of the invention is formed. Such filler particles may be added as ballast and/or may provide the composition with functionality. Non-limiting examples include: zirconium dioxide and barium sulfate to increase radio-opacity, which may be added to smaller particles (e.g. milled) composition of to the invention (including the active ingredient). The amount of added filler particles may be up to about 80 wt %, preferably up to about 40 wt % of the weight of (preferably inorganic) excipient of high mechanical strength.

Compositions of the invention may further comprise particles of:
(i) inert fillers, such as those mentioned hereinbefore;
(ii) excipients (such as porous ceramic materials or geopolymers) in which active ingredient has been pre-loaded (e.g. for sustained release); and/or
(iii) compositions of the invention (i.e. smaller particles), bonded together as part of a larger network comprising the relevant excipient.

Compositions of the invention may alternatively be milled to a fine powder, preferably with a powder grain size of below about 100 μm, and more preferably below about 20 μm. Milling is optionally performed using ball-milling, planetary ball-milling, jet milling or a combination thereof.

Compositions of the invention may also optionally contain bulking agents, porogens, dispersion agents or gelating agents to control the rheology and porosity. The total amount of such excipients is limited to about 20 wt % of the total weight of the composition of the invention. Non-limiting examples of such excipients include polycarboxylic acids, cellulose, polyvinylalchol, polyvinylpyrrolidone, starch, nitrilotriacetic acid (NTA), polyacrylic acids, PEG, sorbitol, mannitol, glycerol, pharmaceutically-acceptable oils (including vegetable oils (olive oil, maize oil, corn oil, peanut oil, sunflower oil, flaxseed oil, palm oil, castor oil, soybean oil, etc.), essential oils (e.g. evening primrose oil), omega 3 oils (e.g. fish oils), paraffin oil, lipid oils derived from animal issue, silicone oils, etc), and combinations thereof.

Additional pharmaceutically-acceptable excipients include carbohydrates and inorganic salts such as sodium chloride, calcium phosphates and calcium carbonate.

The compositions of the invention are preferably administered perorally to the gastrointestinal tract and may provide for controlled release of active ingredient in the stomach and/or, preferably, the intestinal system.

In this respect, the compositions of the invention may be incorporated into various kinds of pharmaceutical preparations intended for peroral administration using standard techniques (see, for example, Lachman et al, "*The Theory and Practice of Industrial Pharmacy*", Lea & Febiger, $3^{rd}$ edition (1986) and "*Remington: The Science and Practice of Pharmacy*", Gennaro (ed.), Philadelphia College of Pharmacy & Sciences, $19^{th}$ edition (1995)).

Pharmaceutical preparations comprising compositions of the invention contain a pharmacologically effective amount of the active ingredient. By "pharmacologically effective amount", we refer to an amount of active ingredient, which is capable of conferring a desired therapeutic effect on a treated patient, whether administered alone or in combination with another active ingredient. Such an effect may be objective (i.e. measurable by some test or marker) or subjective (i.e. the subject gives an indication of, or feels, an effect).

More preferred compositions of the invention may be adapted (for example as described herein) to provide a sufficient dose of drug over the dosing interval (irrespective of the number of doses per unit time) to produce a desired therapeutic effect.

The amounts of active ingredients that may be employed in compositions of the invention may thus be determined by the physician, or the skilled person, in relation to what will be most suitable for an individual patient. This is likely to vary with the route of administration, the type and severity of the condition that is to be treated, as well as the age, weight, sex, renal function, hepatic function and response of the particular patient to be treated.

Suitable dosages of active ingredeient in one oral delivery unit (e.g. one tablet) may be below 1 g, preferably below 100 mg and above 1 pg.

When compositions of the invention comprise opioid analgesics, appropriate pharmacologically effective amounts of such opioid analgesic compounds include those that are capable of producing (e.g. sustained) relief of pain when administered perorally. Thus, the total amount of opioid analgesic active ingredient that may be employed in a composition of the invention will depend upon the nature of the relevant active ingredient that is employed, but may be in the range of about 0.0005%, such as about 0.1% (e.g. about 1%, such as about 2%) to about 20%, such as about 10%, for example about 7%, by weight based upon the total weight of the composition. The amount of this active ingredient may also be expressed as the amount in a unit dosage form. In such a case, the amount of opioid analgesic active ingredient that may be present may be sufficient to provide a dose per unit dosage form that is in the range of between about 1 µg (e.g. about 5 µg) and about 50 mg (e.g. about 15 mg, such as about 10 mg).

The above-mentioned dosages are exemplary of the average case; there can, of course, be individual instances where higher or lower dosage ranges are merited, and such are within the scope of this invention.

Compositions of the invention comprising opioid analgesics are useful in the treatment of pain, particularly severe and/or chronic pain. According to a further aspect of the invention there is provided a method of treatment of pain which method comprises administration of a composition of the invention to a person suffering from, or susceptible to, such a condition.

For the avoidance of doubt, by "treatment" we include the therapeutic treatment, as well as the symptomatic treatment, the prophylaxis, or the diagnosis, of the condition.

Compositions of the invention possess the advantage of the avoidance and/or reduction of the risk of either dose dumping (i.e. the involuntary release), or equally importantly the deliberate ex vivo extraction, of the majority (e.g. greater than about 50%, such as about 60%, for example about 70% and in particular about 80%) of the dose of the active ingredient(s) that is initially within a composition of the invention, either in vivo (i.e. when a composition of the invention is administered to a patient) or ex vivo (i.e. into another medium outside the body), within a timeframe that is likely to give rise to undesirable consequences, such as adverse pharmacological effects (for example when such release occurs in vivo in an involuntary sense), or the potential for abuse of that active ingredient (for example when such release is deliberately effected ex vivo by an individual). Such dose dumping release may for example take place either in vivo or ex vivo within about 3 hours, such as within about 2 hours, for example within about 1 hour, and particularly within about 30 minutes.

Compositions of the invention have the advantage that they provide for improved sustained release properties with minimal risk for severe/lethal side effects (i.e. reduction of dose dumping and/or abuse potential when the active ingredient to be employed is abusable, such as an opioid, a benzodiazepine, etc.). The compositions of the invention may provide protection against intentional mechanical breakdown, e.g. by traditional methods such as crushing, pestle and mortar, hammering etc. by having a high compressive strength level at the micro-level material. This protection may be provided by the composition of the invention as such, and especially when those compositions are employed in conjunction with a carrier or filler that also possesses high mechanical strength.

Compositions of the invention may also have the advantage that they may be prepared using established pharmaceutical processing methods and may employ materials that are approved for use in foods or pharmaceuticals or of like regulatory status.

Compositions of the invention may also have the advantage that they may be more efficacious than, be less toxic than, be longer acting than, be more potent than, produce fewer side effects than, be more easily absorbed than, and/or have a better pharmacokinetic profile than, and/or have other useful pharmacological, physical, or chemical properties over, pharmaceutical compositions known in the prior art, whether for use in the treatment of pain or otherwise.

Wherever the word "about" is employed herein in the context of dimensions (e.g. values, temperatures, pressures (exerted forces), relative humidities, sizes and weights, particle or grain sizes, pore sizes, timeframes etc.), amounts (e.g. relative amounts (e.g. numbers or percentages) of particles, individual constituents in a composition or a component of a composition and absolute amounts, such as doses of active ingredients, numbers of particles, etc.), deviations (from constants, degrees of degradation, etc.) it will be appreciated that such variables are approximate and as such may vary by ±10%, for example ±5% and preferably ±2% (e.g. ±1%) from the numbers specified herein.

The invention is illustrated by the following examples.

General Methodology

Pellets were manufactured by extrusion and spheronization.

Dry excipients, including ceramic materials (aluminium silicate (Halloysite, Premium); China Clays, New Zealand) or calcium aluminate (Doxa AB, Sweden)), pelletisation aid material (microcrystalline cellulose; Avicel® PH101; FMC, USA) and active ingredient (fentanyl free base; Johnson Matthey, Macfarlan Smith, UK) or zolpidem tartrate (Cambrex, USA)) were blended together for 30 minutes in a tumbling mixer.

Kollicoat® MAE 30 DP (BASF, Germany), Eudragit FS 30D (Evonik Degussa GmbH, Germany), or water, was then added to the resultant dry mix as a granulation liquid with continuous mixing in a high-speed mixer.

The wet mass was then extruded at a constant rate into small oblong pieces (extrudates). The extrudates were thereafter spheronized in a spheronizer until round spheres were obtained. The pellets were dried in an oven at 65° C. for 1-3 hours.

Release profiles were measured according United States Pharmacopoeia <711> dissolution paddle method. The paddle rotation rate was 50 rpm and various media (phosphate buffer pH 6.8, 0.1 M HCl solution or ethanol (48%)) with a volume of 200 mL at 37° C. were used. Samples were collected after 15, 30, 60, 120, 180, 240 and 300 minutes and the amount of active ingredient was determined using High Performance Liquid Chromatography (HPLC).

EXAMPLE 1

A batch of 60 g of pellets were prepared (as with all examples described hereinafter, according to the general methodology described above) using 47.2 g of aluminium silicate (Halloysite), employing 0.8 g of fentanyl base as the active ingredient, 12 g of microcrystalline cellulose as a pelletisation aid material, and 64 g of Kollicoat MAE 30 DP as the granulation liquid.

These pellets were also milled by hand with a pestle and mortar to a smaller size than the original pellets.

EXAMPLE 2 (COMPARATIVE EXAMPLE)

A batch of 60 g of pellets were prepared using 47.2 g of aluminium silicate (Halloysite), 0.8 g of fentanyl base, 12 g of microcrystalline cellulose and 33 g of purified water as the granulation liquid.

EXAMPLE 3

A batch of 60 g of pellets were prepared using 47.2 g of calcium aluminate, 0.8 g of fentanyl base, 12 g of microcrystalline cellulose and 34 g of Kollicoat MAE 30 DP.

EXAMPLE 4 (COMPARATIVE EXAMPLE)

A batch of 60 g of pellets were prepared using 38.2 g of calcium aluminate, 0.8 g of fentanyl base, 21 g of microcrystalline cellulose and 33 g of purified water.

EXAMPLE 5

A batch of 60 g of pellets were prepared using 47.2 g of aluminium silicate (Halloysite), 0.8 g of zolpidem tartrate as the active ingredient, 12 g of microcrystalline cellulose and 84 g of Kollicoat MAE30DP.

EXAMPLE 6 (COMPARATIVE EXAMPLE)

A batch of 60 g of pellets were prepared using 47.2 g of aluminium silicate (Halloysite), 0.8 g of zolpidem tartrate, 12 g of microcrystalline cellulose and 44 g of purified water.

EXAMPLE 7

A batch of 60 g of pellets were prepared using 47.2 g of aluminium silicate (Halloysite), 0.8 g of zolpidem tartrate, 12 g of microcrystalline cellulose and 87 g of Eudragit FS30D.

EXAMPLE 8 (COMPARATIVE EXAMPLE)

A batch of 60 g of pellets were prepared using 38.2 g of aluminium silicate (Halloysite), 0.8 g of fentanyl base, 21 g of microcrystalline cellulose and 41 g of purified water. These pellets were milled by hand with a pestle and mortar to a smaller size than the original pellets.

Release Profiles Of Formulations Of Examples 1 to 8

FIG. 1 shows the release profile of the active ingredient from pellets prepared by way of Examples 1 and 2 in phosphate buffer (pH 6.8). The release of fentanyl was slower from pellets in which Kollicoat was employed as the granulation liquid as compared to water.

Figure 2:
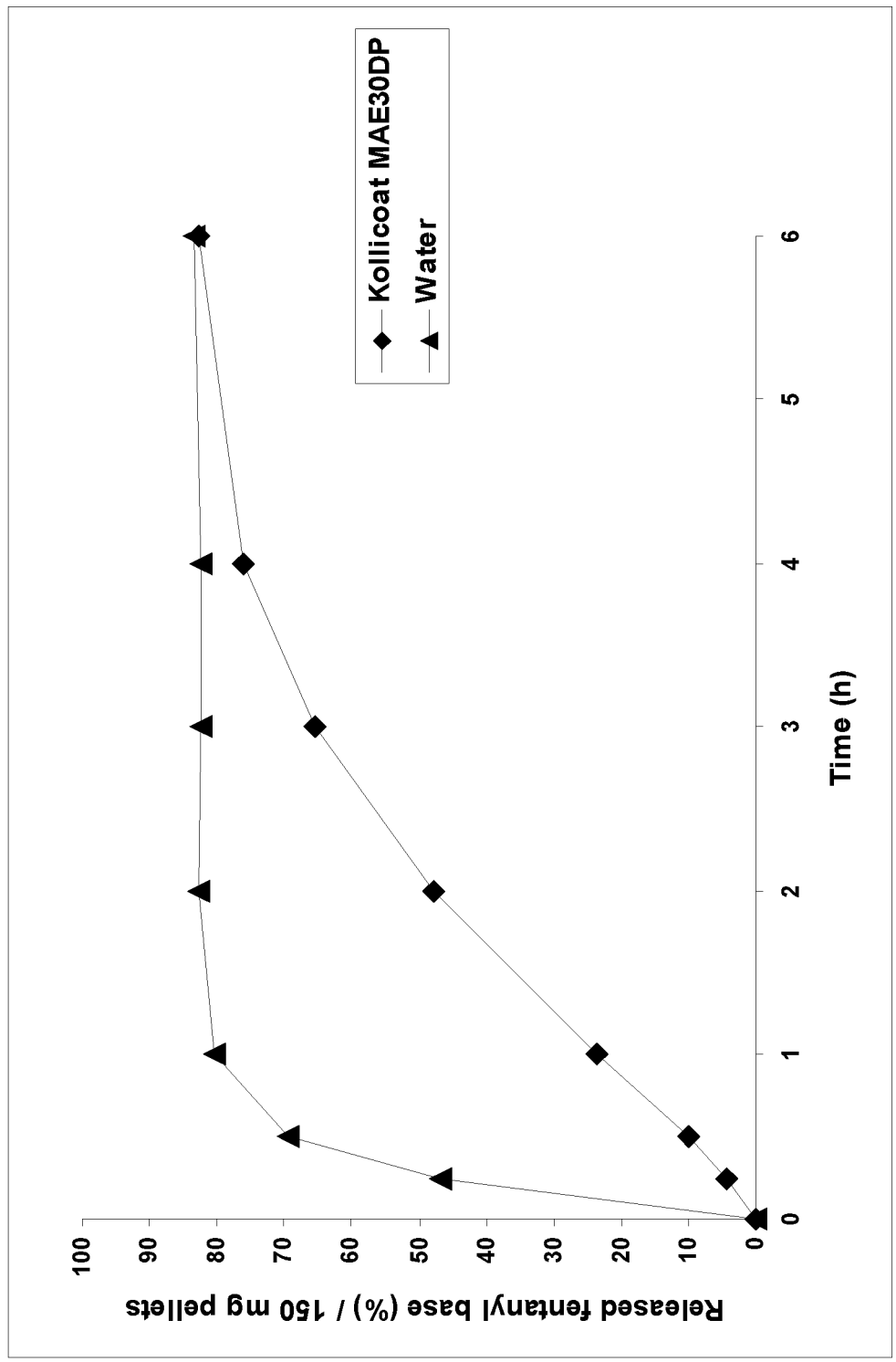
FIG. 2 shows the release profile of fentanyl base in ethanol (48%) from ceramic pellets made from calcium aluminate, employing either Kollicoat MAE 30 DP or water as the granulation liquid.

FIG. 2 shows the release profile of the active ingredient from pellets prepared by way of Examples 3 and 4 in 48% ethanol. Drug release in ethanol was considerably faster for pellets made using water as the granulation liquid, when compared to pellets made with Kollicoat.

Figure 3:
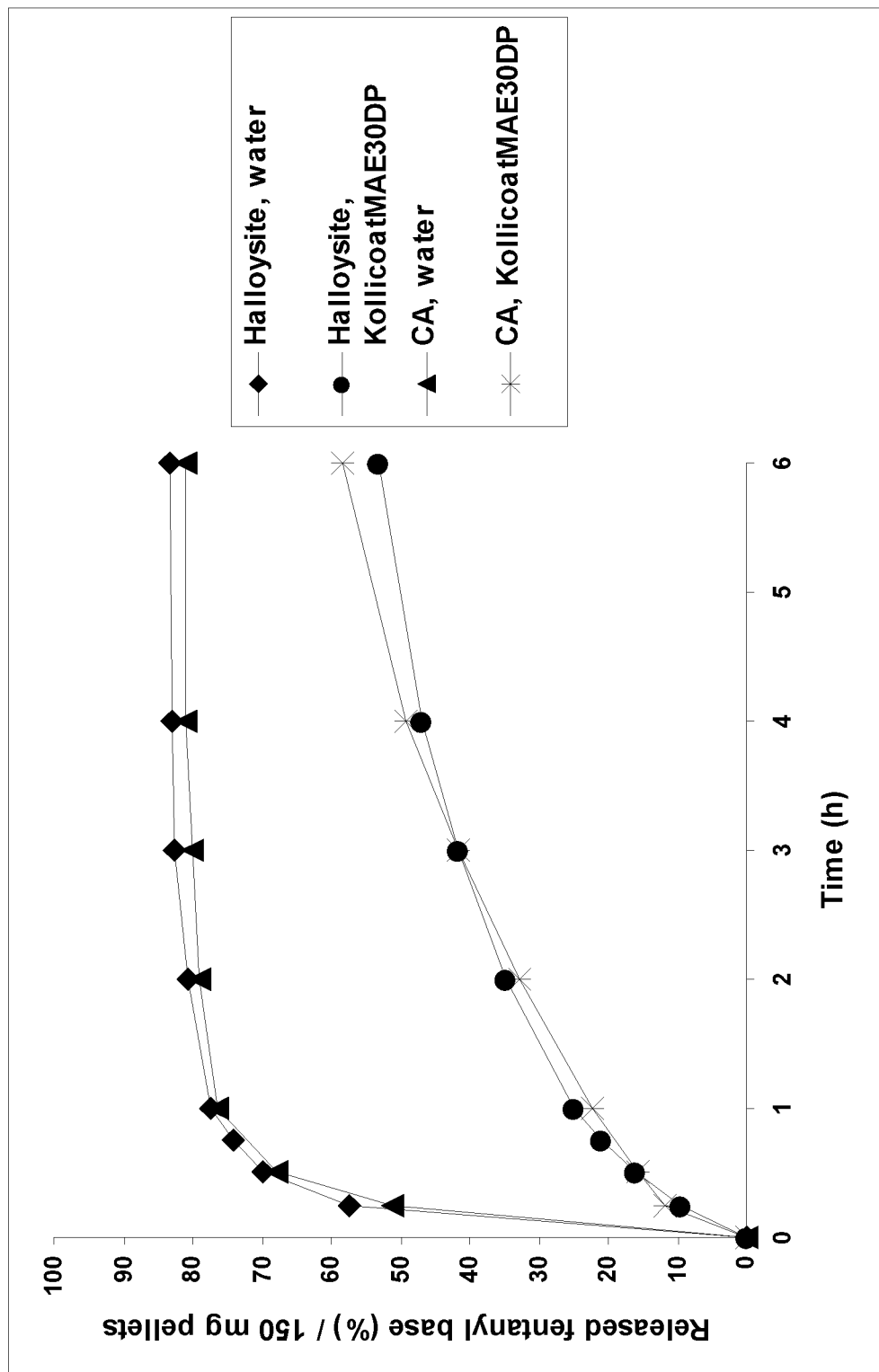
FIG. 3 shows the release profile of fentanyl base in 0.1 M HCl (pH 1) from ceramic pellets made from aluminium silicate (halloysite), employing either Kollicoat MAE 30 DP or water as the granulation liquid.

FIG. 3 shows the release profile of the active ingredient from pellets prepared by way of Examples 1, 2, 3 and 4 in 0.1 M HCl (pH 1). Drug release in 0.1 M HCl was considerably faster for pellets made using water as the granulation liquid, when compared to pellets made with Kollicoat.

Figure 4:
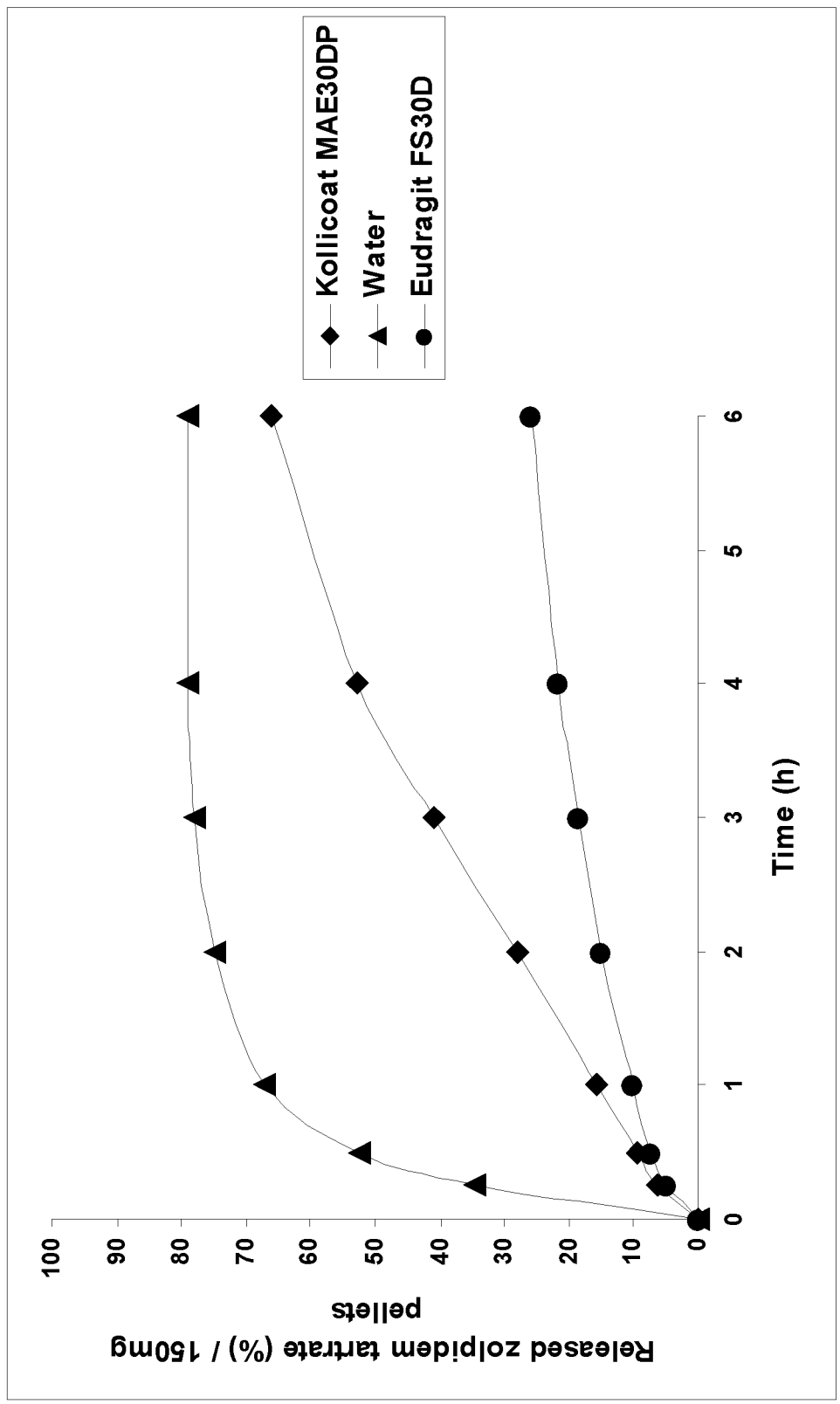
FIG. 4 shows the release profile of zolpidem tartrate in phosphate buffer (pH 6.8) from ceramic pellets made from aluminium silicate (halloysite), employing either Kollicoat MAE30DP, Eudragit FS30D or water as the granulation liquid.
Figure 5:
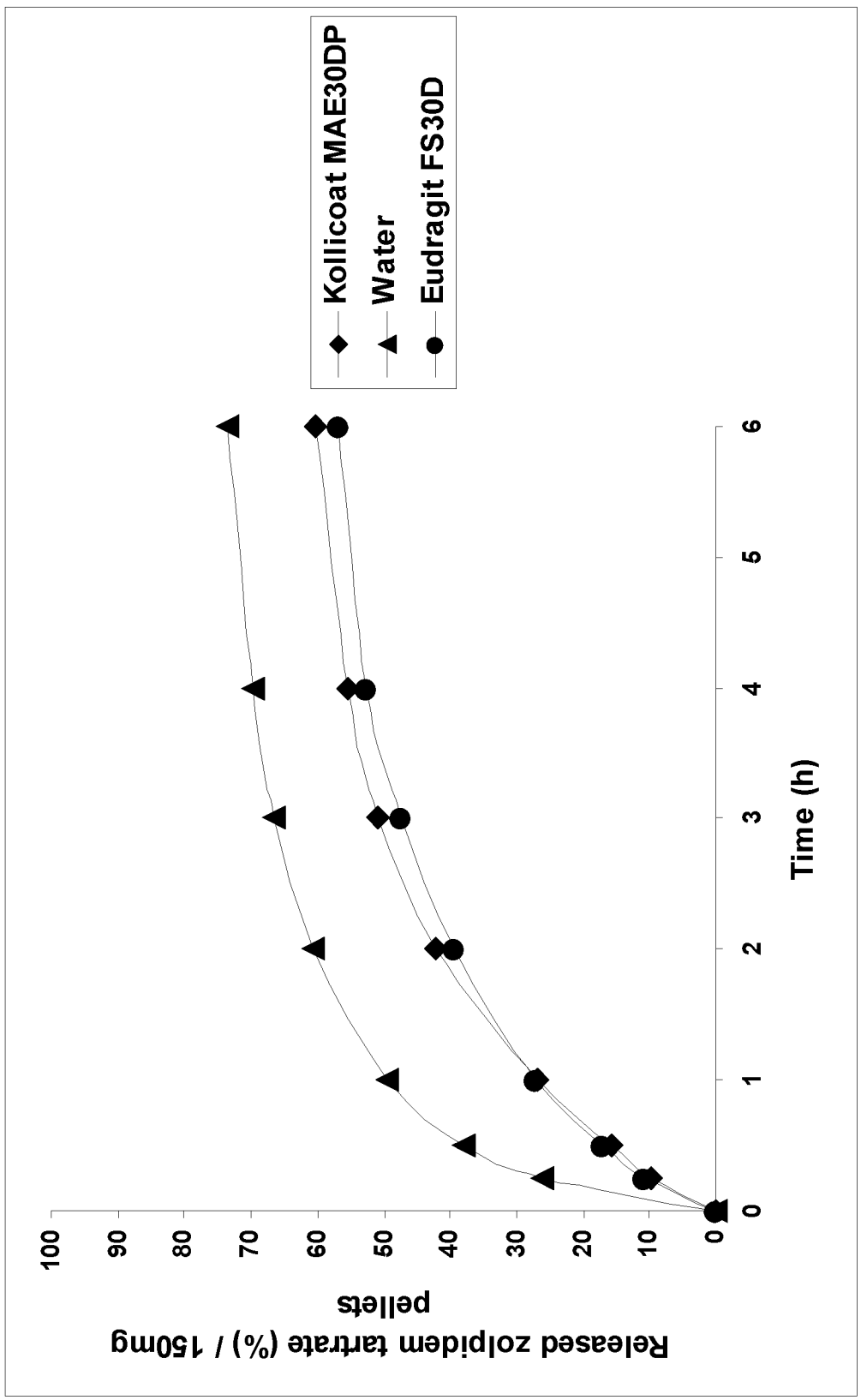
FIG. 5 shows the release profile of zolpidem tartrate in ethanol (48%) from ceramic pellets made from aluminium silicate (halloysite), employing either Kollicoat MAE30DP, Eudragit FS30D or water as the granulation liquid.

FIGS. 4 and 5 show the release profile of the active ingredient from pellets prepared by way of Examples 5, 6 and 7 in phosphate buffer (pH 6.8) (FIG. 4) and 48% ethanol (FIG. 5). These figures show that the drug release from these pellets was slower in the two media when using both Kollicoat MAE30DP and Eudragit FS30D as the granulating liquid as compared to water.

Figure 6:
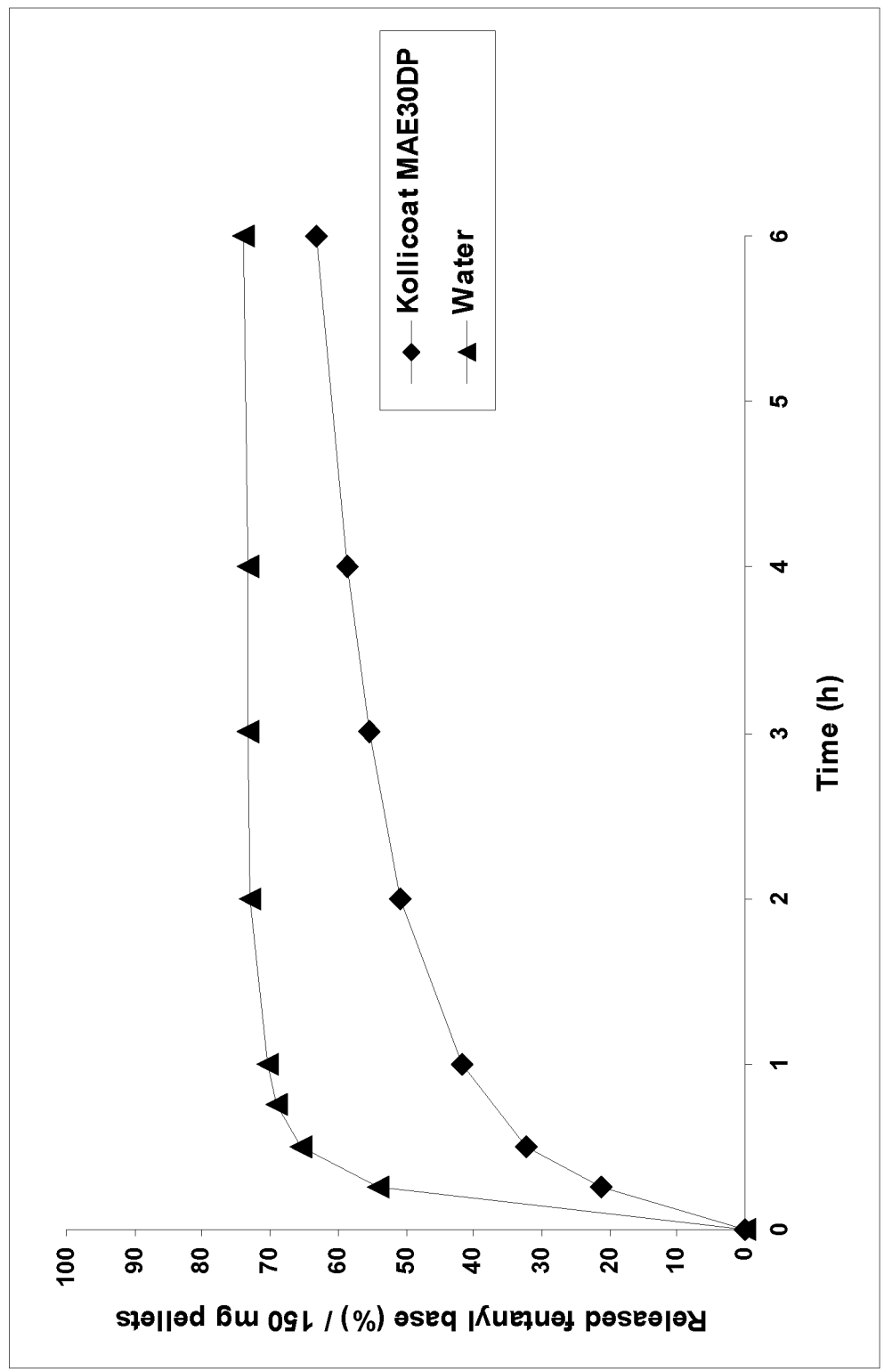
FIG. 6 shows the release profile of fentanyl base in phosphate buffer (pH 6.8) from milled ceramic pellets made from aluminium silicate (halloysite), employing either Kollicoat MAE 30 DP or water as the granulation liquid.

FIG. 6 shows the release profile of the active ingredient from milled pellets prepared by way of Examples 1 and 8 in phosphate buffer (pH 6.8) and 48% ethanol. These figures show that the drug release from these pellets was slow in both buffer and ethanol.

EXAMPLE 9

The purpose of this experiment was to evaluate release from pellets in a warm media, buffer pH 6.8.

Two batches of pellets, one in accordance with the invention (a; 75 g), and one not in accordance with the invention (b; 27.7 g), were prepared as described in the general methodology section above, comprising:

(a) 47.2 g of aluminium silicate (Halloysite), 0.8008 g of zolpidem tartrate as the active ingredient, 12.0 g of microcrystalline cellulose and 84.4 g of Kollicoat MAE30DP; and (b) 38.2 g of aluminium silicate (Halloysite), 0.8002 g of zolpidem tartrate as the active ingredient, 21.0 g of microcrystalline cellulose and 43.87 g of water.

About 150 mg samples of the pellets were placed in a 250 mL beaker containing 200 mL of pre-warmed phosphate buffer pH 6.8. The beaker was placed on a hot stirrer plate and a magnetic stirrer was used during the experiment.

The temperature of the phosphate buffer was measured at time 0, 10 and 30 minutes and samples were taken from the beaker at 10 and 30 minutes, respectively, and thereafter analyzed chromatographically with HPLC.

The measured temperatures are tabulated in Table 1 below.

TABLE 1

| Sample | Amount pellets (mg) | Temp (° C.) (0 min) | Temp (° C.) (10 min) | Temp (° C.) (30 min) |
|---|---|---|---|---|
| (a) | | | | |
| Batch 1 | 151.6 | 79.3 | 80.5 | 76.6 |
| Batch 2 | 155.5 | 64.6 | 58.5 | 51.7 |
| Batch 3 | 150.4 | 64.0 | 87.0 | 78.1 |
| Batch 4 | 151.8 | 59.0 | 48.7 | 39.8 |
| (b) | | | | |
| Batch 1 | 150.7 | 67.5 | 73.8 | 77.3 |
| Batch 2 | 153.8 | 62.3 | 53.1 | 50.1 |
| Batch 3 | 151.5 | 73.0 | 76.8 | 77.0 |
| Batch 4 | 152.9 | 68.0 | 56.8 | 43.9 |

Figure 7:
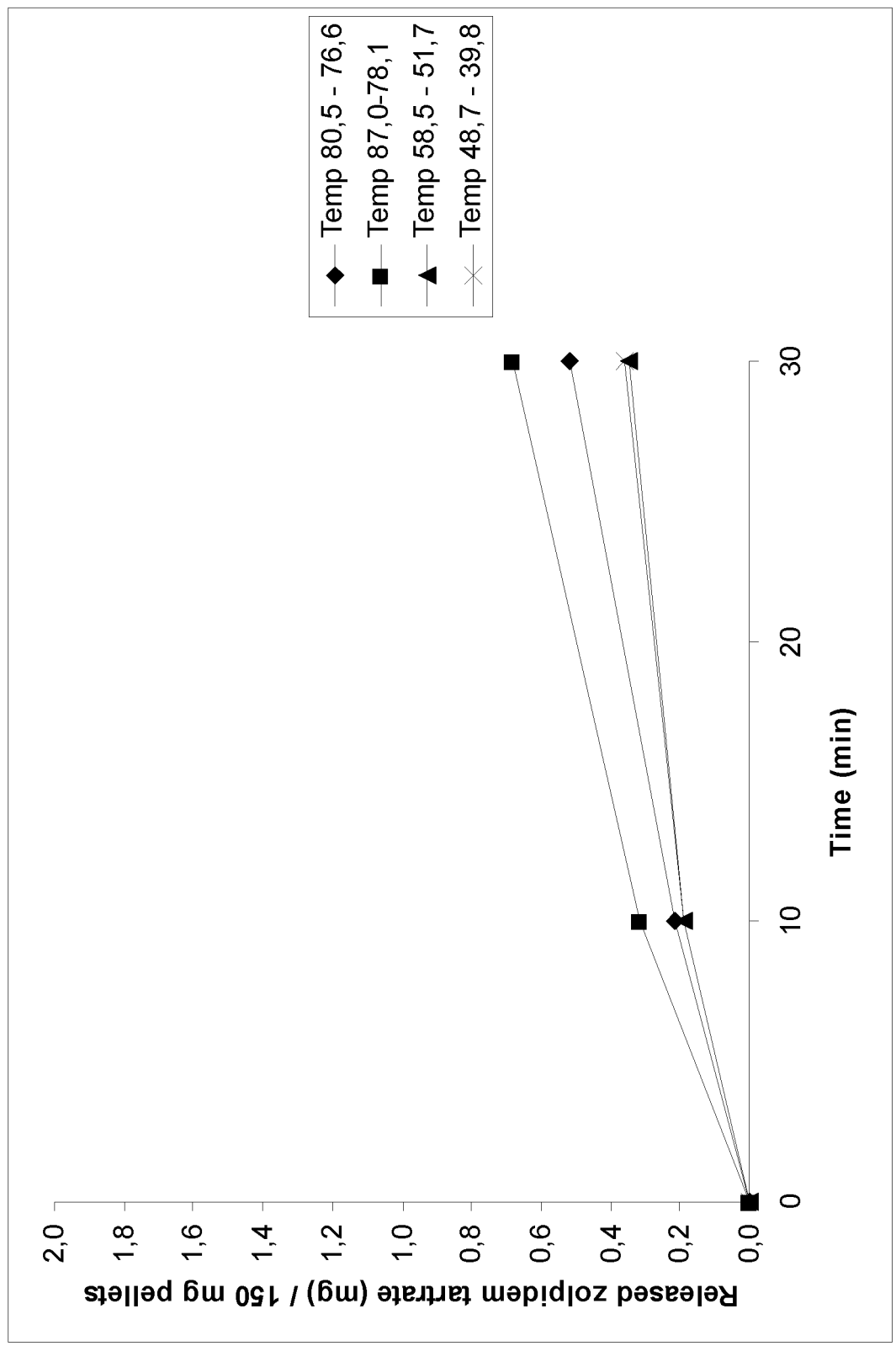
FIGS. 7 and 8 show the release profiles at elevated temperature of the zolpidem tartrate in phosphate buffer (pH 6.8) from pellets made from aluminium silicate (halloysite), employing either Kollicoat MAE 30 DP (FIG. 7) or water (FIG. 8) as the granulation liquid.

FIG. 7 shows the release profile of the zolpidem from pellets prepared by way of Example 9 in phosphate buffer (pH 6.8) from each of Batches 1 to 4 of pellets (a) (prepared in accordance with the invention).

Figure 8:
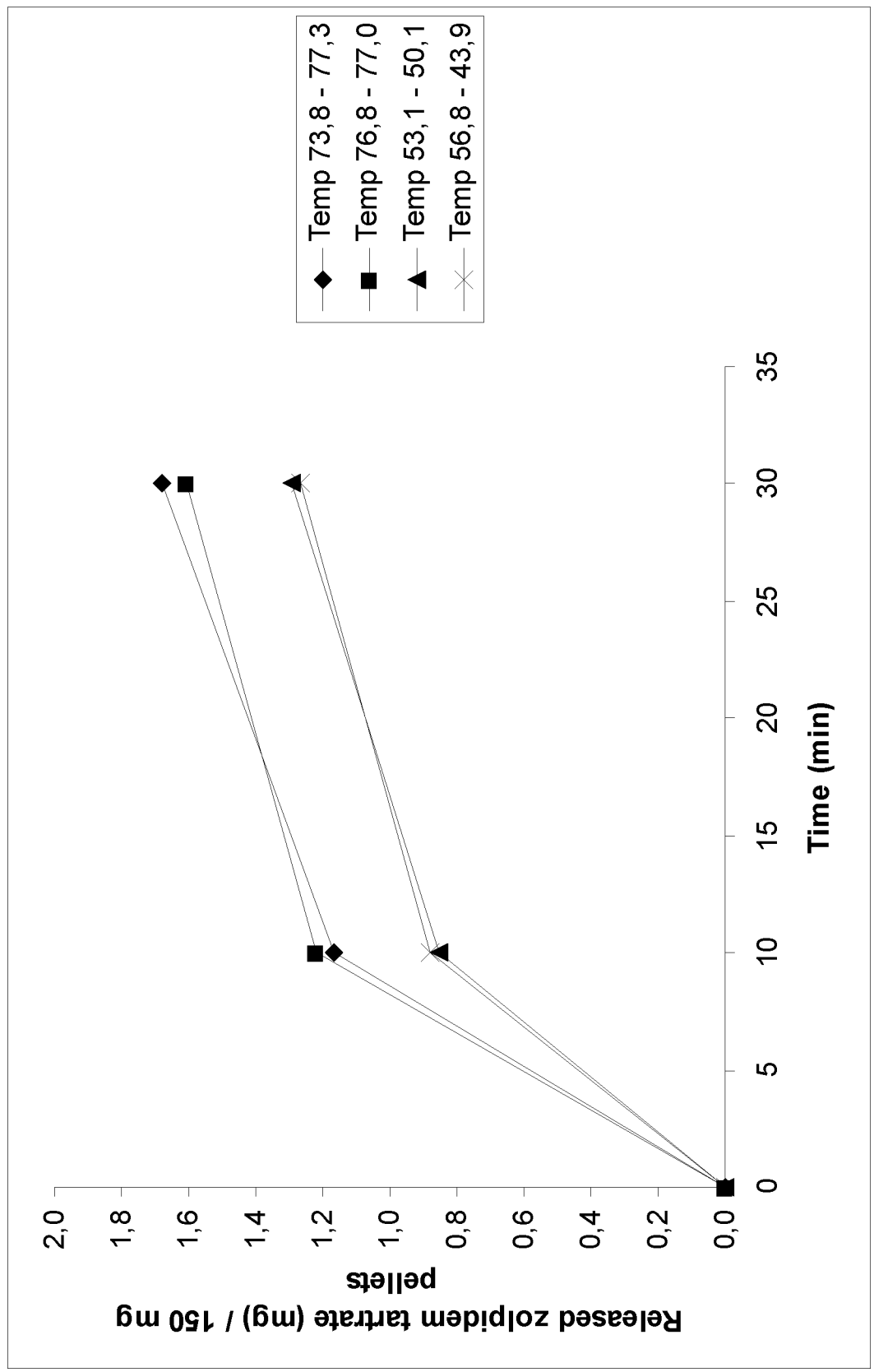

FIG. 8 shows the release profile of the zolpidem from pellets prepared by way of Example 9 in phosphate buffer (pH 6.8) from each of Batches 1 to 4 of pellets (b) (not prepared in accordance with the invention).

Figure 9:
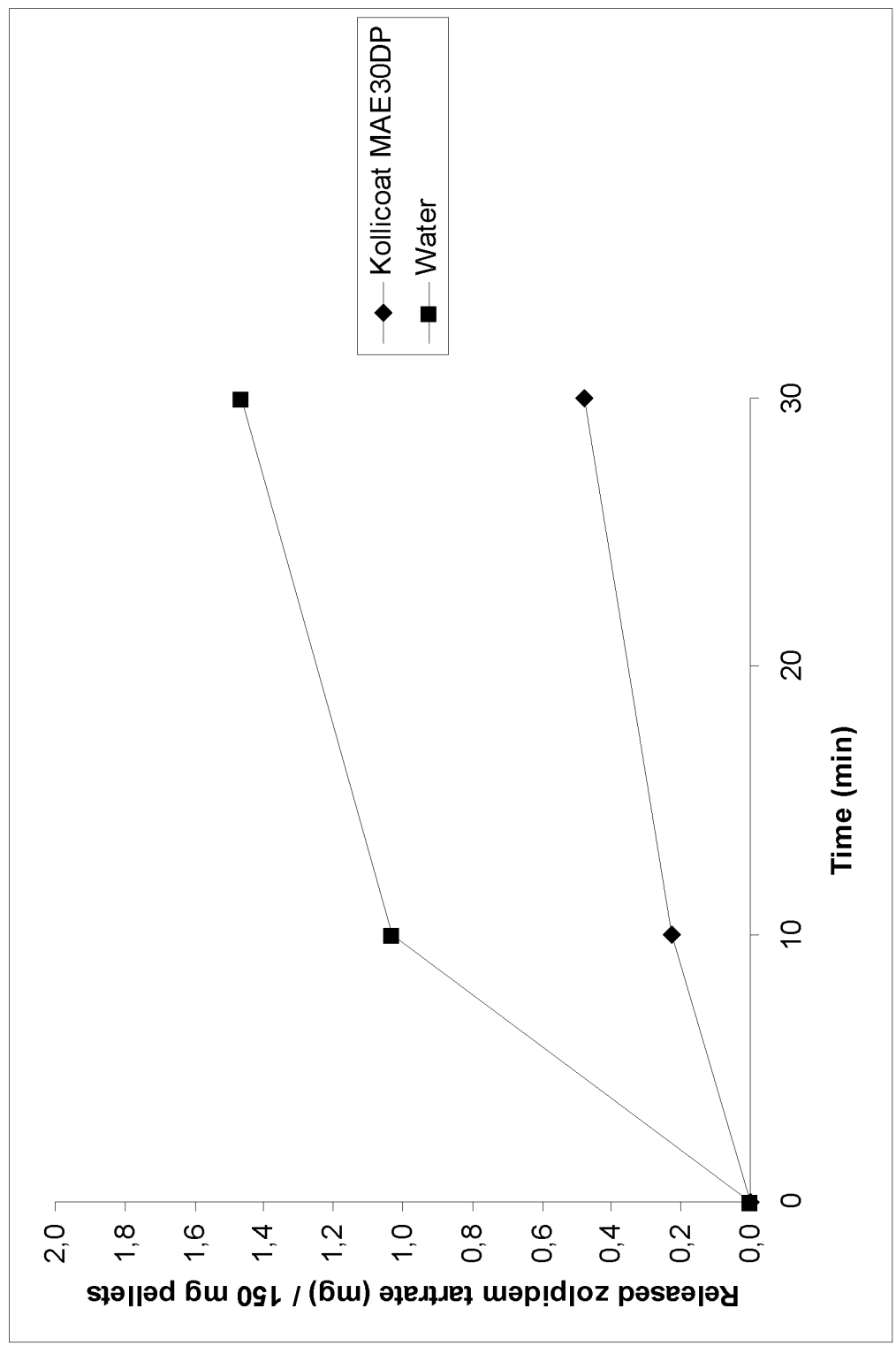
FIG. 9 shows the mean values from FIGS. 7 (lower profile) and 8 (upper profile) respectively.

FIG. 9 shows the mean values from FIGS. 7 (lower profile) and 8 (upper profile) respectively.

Figure 10:
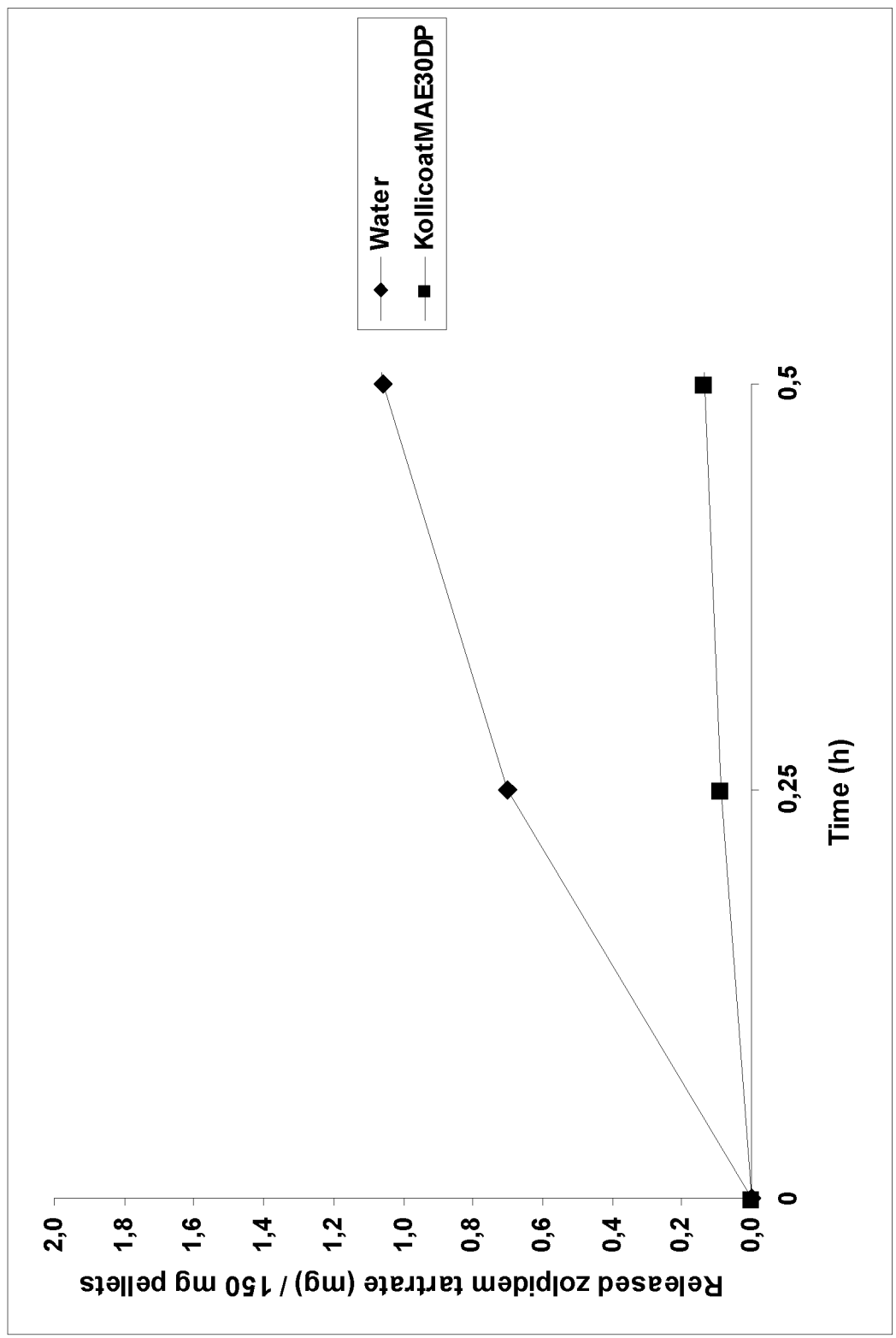
FIG. 10 shows the release profiles at 37° C. of zolpidem tartrate in phosphate buffer (pH 6.8) from pellets made from aluminium silicate (halloysite), employing either Kollicoat MAE 30 DP (lower profile) or water (upper profile) as the granulation liquid.

FIG. 10 shows the release profile of zolpidem from pellets prepared by way of Example 9 in phosphate buffer (pH 6.8) at about 37° C. from pellets (a) (lower profile) and (b) (upper profile), respectively.

Taken together, these figures show that drug release from pellets prepared in accordance with the invention is much slower in all cases.

The above examples show that, by employing a film-forming agent as part of a granulation liquid, it is possible to obtain sustained release of the active substance in buffer, ethanol and at low pH. Further, the release profile is less affected by milling when compared to pellets that have been made with water as the granulation liquid.

The invention claimed is:

1. A sustained-release pharmaceutical composition comprising a solid, continuous network with a high mechanical strength, which network comprises an excipient, which network also comprises secondary pores, within which secondary pores is interspersed a mixture of an active ingredient and a film-forming agent, wherein the secondary pores are formed by physically and/or chemically bonding together the surfaces of particles of the excipient in the presence of said mixture, characterised in that said secondary pores are formed during the production of the composition wherein the excipient is based on one or more ceramic materials or one or more geopolymeric materials or combinations thereof.

2. The composition as claimed in claim 1 wherein the excipient is inorganic.

3. The composition as claimed in claim 1 wherein the active ingredient that is employed is an opioid analgesic.

4. The composition as claimed in claim 3, wherein the opioid analgesic is a morphinan derivative, a benzomorphan derivative, a phenylpiperidine, a phenylheptamine, an open chain compound, a diphenylpropylamine derivative, a mixed agonist/antagonist or another synthetic opioid.

5. The composition as claimed in claim 3, wherein the opioid analgesic is selected from morphine, codeine, thebaine or a Diels-Alder adduct thereof, diamorphine, hydromorphone, oxymorphone, hydrocodone, oxycodone, etorphine, nicomorphine, hydrocodeine, dihydrocodeine, metopon, normorphine, N-(2-phenylethyl)normorphine, racemorphan, levorphanol, dextromethorphan, levallorphan, cyclorphan, butorphanol, nalbufine, cyclazocine, pentazocine, phenazocine, pethidine (meperidine), fentanyl, alfentanil, sufentanil, remifentanil, ketobemidone, carfentanyl, anileridine, piminodine, ethoheptazine, alphaprodine, betaprodine, 1-methyl-4-phenyl-1,2,3,6-tetrahydropyridine, diphenoxylate, loperamide, methadone, isomethadone, propoxyphene, levomethadyl acetate hydrochloride, dextromoramide, piritramide, bezitramide, dextropropoxyphene, buprenorphine, nalorphine, oxilorphan, tilidine, tramadol, allylprodine, benzylmorphine, clonitazene, desomorphine, diampromide, dihydromorphine, dimenoxadol, dimepheptanol, dimethylthiambutene, dioxaphetyl butyrate, dipipanone, eptazocine, ethylmethylthiambutene, ethylmorphine, etonitazene, hydroxypethidine, levophenacylmorphan, lofentanil, meptazinol, metazocine, myrophine, narceine, norpipanone, papvretum, phenadoxone, phenomorphan, phenoperidine, propiram and dezocine.

6. The composition as claimed in claim 5, wherein the opioid analgesic is selected from buprenorphine, alfentanil, sufentanil, remifentanil and fentanyl.

7. The composition as claimed in claim 6, wherein the opioid analgesic is fentanyl.

8. The composition as claimed in claim 1, wherein the ceramic material is a calcium aluminate or an aluminium silicate.

9. The composition as claimed in claim 1, wherein the ceramic material is a halloysite.

10. The composition as claimed in claim 1 wherein the grain size of the excipient is below about 20 µm.

11. The composition as claimed in claim 1 wherein the film-forming agent is an enteric coating material.

12. The composition as claimed in claim 11, wherein the film-forming agent is a copolymer derived from methacrylic acid and ethyl acrylate or a neutral methacrylic polymer.

13. The composition as claimed in claim 1 which further comprises a pelletisation aid material.

14. The composition as claimed in claim 13 wherein the pelletisation aid material is microcrystalline cellulose.

15. A process for the preparation of a composition as defined by claim 1 which comprises mixing together the excipient and the active ingredient, and then adding the film-forming agent along with, or in, a liquid, so providing a wet granulate.

16. The process as claimed in claim 15 which further comprises:
    (I) extrusion of the granulate;
    (II) spheronisation;
    (III) drying; and/or
    (IV) hardening.

17. A composition obtainable by the process as defined in claim 15.

18. A process for the preparation of a composition as defined in claim 1 which comprises:
    mixing together an excipient and an active ingredient; and
    adding a film-forming agent along with, or in, a liquid, so providing a wet granulate, and thereby forming a solid, continuous network with a high mechanical strength and also thereby forming secondary pores in said network, wherein said active ingredient and film-forming agent are interspersed within said secondary pores.

19. A method of treatment of pain which comprises administration of a composition as defined in claim 3, to a person suffering from, or susceptible to, such a condition.

* * * * *